United States Patent [19]
Houston, Jr. et al.

[11] Patent Number: 5,824,483
[45] Date of Patent: Oct. 20, 1998

[54] CONFORMATIONALLY-RESTRICTED COMBINATORIAL LIBRARY COMPOSITION AND METHOD

[75] Inventors: Michael E. Houston, Jr.; Robert S. Hodges, both of Edmonton, Canada

[73] Assignee: Pence Inc., Edmonton, Canada

[21] Appl. No.: 491,527

[22] Filed: Jun. 16, 1995

Related U.S. Application Data

[63] Continuation-in-part of Ser. No. 260,199, Jun. 15, 1994, Pat. No. 5,738,996, and Ser. No. 245,507, May 18, 1994, abandoned.

[51] Int. Cl.$^6$ .................................................... G01N 33/53
[52] U.S. Cl. ........................... 435/7.1; 436/501; 436/518; 436/531; 436/543
[58] Field of Search ............................ 435/7.1; 436/501, 436/518, 531, 543

[56] References Cited

U.S. PATENT DOCUMENTS

| | | |
|---|---|---|
| 5,182,366 | 1/1993 | Huebner et al. . |
| 5,266,684 | 11/1993 | Rutter et al. . |
| 5,565,325 | 10/1996 | Bloks ......................................... 435/2.1 |

FOREIGN PATENT DOCUMENTS

| | | |
|---|---|---|
| WO 86/00991 | 2/1986 | WIPO . |
| WO 92/09300 | 6/1992 | WIPO . |
| WO 93/15110 | 8/1993 | WIPO . |
| WO 94/28028 | 12/1994 | WIPO . |

OTHER PUBLICATIONS

Gilon, C., et al., "Backbone Cyclization: A New Method for Conferring Conformational Restraint on Peptides," *Biopolymers* 31:745–750 (1991).

Moore, G.J., "Designing Peptide Mimetics," *TiPS* 15:124–129 (1994).

Weinstein, B., Ed., "Peptide Backbone Modifications," in *Chemistry and Biochemistry of Amino Acids, Peptides, and Proteins*, vol. 7 Marcel Dekker, Inc., New York, NY, Chapter 5, pp. 267 (1983).

Alper, J., "Drug Discovery on the Assembly Line," *Science* 264:1399–1401 (1994).

Barbas, C.F., III, et al., "Semisynthetic Combinatorial Antibody Libraries: A Chemical Solution to the Diversity Problem," *Proc. Natl. Acad. Sci. USA* 89:4457–4461 (1992).

Brummel, C., et al., "A Mass Spectrometric Solution to the Address Problem of Combinatorial Libraries," *Science* 264:399–402 (1994).

Chang, H.–C., et al., "A General Method for Facilitating Heterodimeric Pairing Between Two Proteins: Application to Expression of $\alpha$ and $\beta$ T–Cell Receptor Extracellular Segments," *Proc. Natl. Acad. Sci. USA* 91:11408–11412 (1994).

Dooley, C.T., et al., "Acetalins: Opioid Receptor Antagonists Determined Through the Use of Synthetic Peptide Combinatorial Libraries," *Proc. Natl. Acad. Sci. USA* 90:10811–10185 (1993).

Dooley, C.T., and Houghten, Jr., R.A., "The Use of Positional Scanning Synthetic Peptide Combinatorial Libraries for the Rapid Determination of Opioid Receptor Ligands," *Life Sciences* 52(18):1509–1517 (1993).

(List continued on next page.)

*Primary Examiner*—Lora M. Green
*Attorney, Agent, or Firm*—Charles K. Sholtz; Peter J. Dehlinger; Dehlinger & Associates

[57] ABSTRACT

Combinatorial libraries of different-sequence peptide members is disclosed. The libraries are comprised of stabilized, alpha-helical polypeptides having a similar tertiary structure but different amino acid residues at specific, "variable" positions in the sequence. The polypeptides are stabilized through coiled-coil interactions with other $\alpha$-helical polypeptides and/or via intrahelical lactam bridges. Also disclosed are methods for using such libraries to screen for selected macromolecular ligands.

13 Claims, 12 Drawing Sheets

OTHER PUBLICATIONS

Ecker, D.J., et al., "Rational Screening of Oligonucleotide Combinatorial Libraries for Drug Screening," *Nucleic Acids Research* 21(8):1853–1856 (1993).

Eichler, J., and Houghten, R.A., Jr., "Identification of Substrate–Analog Trypsin Inhibitors Through the Screening of Synthetic Peptide Combinatorial Libraries," *Biochemistry* 32:11035–11041 (1993).

Fodor, S.P.A., et al., "Light–Directed, Spatially Addressable Parallel Chemical Synthesis," *Science* 354:767–773 (1991).

Furka, A., "General Method for Rapid Synthesis of Multicomponent Peptide Mixture," *Int. J. Peptide Protein Res.* 37:487–493 (1991).

Houghten, R.A., et al., "Generation and Use of Synthetic Peptide Combinatorial Libraries for Basic Research and Drug Discovery," *Nature* 354:84–86 (1991).

Houghten, R.A., "Finding the Needle in the Haystack," *Current Biology* 4(6):564–567 (1994).

Lam, K.S., et al., "A New Type of Synthetic Peptide Library for Identifying Ligand–Binding Activity," *Nature* 354:82–84 (1991).

Lam, K.S., et al., "Discovery of D–Amino–Acid–Containing Ligands with Different Motifs," *Gene* 137:13–16 (1993).

Lam, K.S., et al., "Treatment of B–Cell Lymphoma Using Peotides," *The Western Journal of Medicine* 158(5):475–479 (1993).

Lam, K.S., and Legl, M. et al., "Streptavidin and Avidin Recognize Peptide Ligands with Different Motifs," *Immunomethods* 1:11–15 (1992).

Needels, M.C., et al., "Generation and Screening of an Oligonucleotide–Encoded Synthetic Peptide Library," *Proc. Natl. Acad. Sci. USA* 90:10700–10704 (1993).

Pinella, C., et al., "Synthetic Peptide Combinatorial Libraries (SPCLs): Identification of the Antigenic Determinant of β–Endorphin Recognized by Monoclonal Antibody 3E7," *Gene* 138:71–76 (1993).

Wong, W.Y., et al., "Representative Combinatorial Peptide Libraries: an Approach to Reduce both Synthesis and Screening Efforts," *Methods in Enzymol.* 6:404–410 (1994).

Perez–Paya et al., J. Biol Chem., vol. 271, #8, pp. 4120–4126 (1996).

Hodges, Biochen. Cell. Biol., vol. 74, pp. 133–154 (1996).

Houston et al., J. Mol. Biol. vol. 262, pp. 270–282 (1996).

Homodimers | Heterodimers
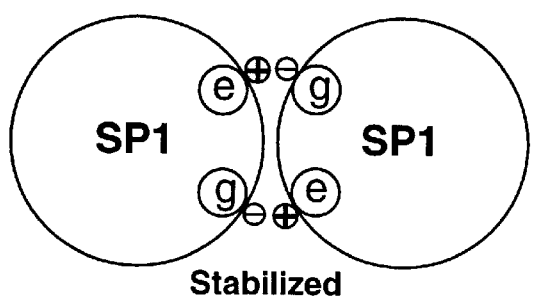
Fig. 2A — Stabilized
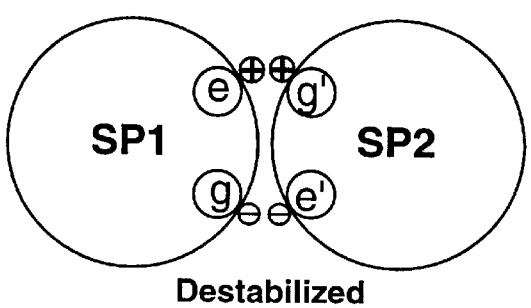
Fig. 2B — Destabilized
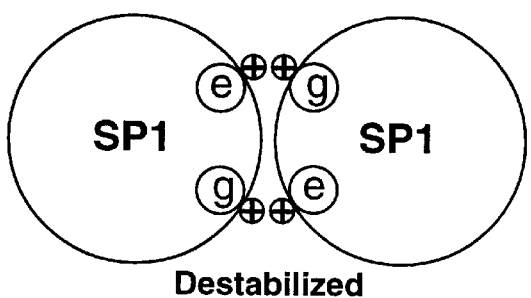
Fig. 2C — Destabilized
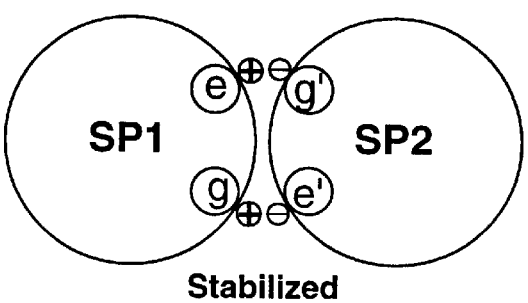
Fig. 2D — Stabilized
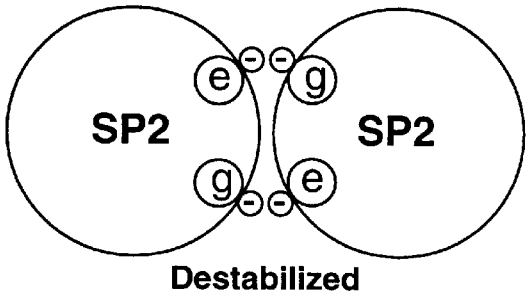
Fig. 2E — Destabilized

```
                     1    3    7    10   13   17   20   24
SEQ ID NO: 12      Ac-EIEALKKEIHFLVQKIHALEKEIK-amide
Coiled-Coil SEQ ID NO: 13      Ac-EAEAAKKEAHFAVQKAHAAEKEAK-amide
Single-Stranded SEQ ID NO: 14              Ac-KHFLVQHTHTG-amide
Linear ZnF Antibody Binding              HF--VQ--H
Residues
```

Fig. 9

```
AAA X₄ X₅ X₆          X₁ X₂ X₃ AAA
AAR X₄ X₅ X₆          X₁ X₂ X₃ AAR
ARA X₄ X₅ X₆          X₁ X₂ X₃ ARA
       ·                     ·
       ·                     ·
       ·                     ·
VVV X₄ X₅ X₆          X₁ X₂ X₃ VVV
```

CONFORMATIONALLY-RESTRICTED COMBINATORIAL LIBRARY COMPOSITION AND METHOD

This application is a continuation-in-part of patent application Ser. No. 08/260,199, filed Jun. 15, 1994, now U.S. Pat. No. 9,738,996, incorporated herein by reference. This application is also a continuation-in-part of patent application Ser. No. 08/245,507, filed May 18, 1994, now abandoned, incorporated herein by reference.

FIELD OF THE INVENTION

The present invention relates to combinatorial libraries of conformationally-restricted polypeptides and methods of screening such libraries.

REFERENCES

Aosaki and Kasai, *Pflugers Arch.* 414: 150–156 (1989).
Barbas, C. F., et al., *Proc. Natl. Acad. Sci. USA* 89(10): 4457 (1992).
Chen, Y.-H., et al., *Biochemistry* 11: 4120–4131 (1972).
Chen, Y.-H., et al., *Biochemistry* 13: 3350–3359 (1974).
Dooley, C. T., et al., *Proc. Natl. Acad. Sci. USA* 90(22): 10822 (1993a).
Dooley, C. T., et al., *Life Sci.* 52(18): 1509 (1993b).
Ecker, D. J., et al., *Nuc. Acids Res.* 21(8): 1853 (1993).
Eichler, J., et al., *Biochemistry* 32(41): 11035 (1993).
Engel, M., et al., *Biochemistry* 30: 3161–3169 (1991).
Farmer, P. S., "Bridging the gap between bioactive peptides and nonpeptides: some perspectives in design" in *DRUG DESIGN,* Ariens, E. J., Ed., Academic Press, New York, Vol. X pp. 119–143 (1980).
Felici, F., et al., *J. Mol. Biol.* 222: 301–310 (1991).
Felix, A. M., et al., *Int. J. Peptide Protein Res.* 31: 231–238 (1988).
Gallop, M., et al., *J. Med. Chem.* 37: 1233–1251 (1994).
Geysen, M. and T. J. Mason, *Bioorg. Med. Chem. Lett.* 3: 397–404 (1993).
Goodman, M. and Listowsky, I., *J. Am. Chem. Soc.* 84: 3370–3371 (1962).
Goodman, M., et al., *Biopolymers* 10: 1719–1730 (1971).
Hodges, R. S., et al., *Peptide Res.* 1: 19–30 (1988).
Hodges, R. S., et al., *Peptide Res.* 3: 123–137 (1990).
Holm, A., and Meldal, M., "Multiple Column Peptide Synthesis" in *PEPTIDES* 1988 (Bayer, et al., Eds., Walter deGruyter & Co., Berlin-N.Y.) p. 208 (1989).
Houghten, R. A., et al., *Nature* 354: 84–86 (1991).
Houghten, R. A., et al., *BioTechniques* 13: 412–421 (1992).
Houghten, R. A., *Current Biology* 4: 564 (1994).
Hruby, V. J., *Biopolymers* 33: 1073–1082 (1993).
Kim, C. A. and J. M. Berg, *Nature* 362: 267–270 (1993).
Kramer, A., et al., *Pept. Res.* 6(6): 314 (1993).
Krizek, B. A., et al., *J. Am. Chem. Soc.* 113: 4518–4523 (1991).
Lam, K. S., et al., *Nature* 354: 82–84 (1991).
Lau, S. Y. M., et al., *J. Chromatogr.* 317: 1229–140 (1984).
Lehrman, R. S., et al., *Biochemistry* 29: 5590–5596 (1990).
McClesky, E. W., et al., *Proc. Natl. Acad. Sci. USA* 84: 4328–4331 (1987).
Meienhofer, J., et al., *Int. J. Pept. Protein Res.* 13: 35–42 (1979).
Meldal, M., et al., *Int. J. Peptide & Protein Res.* 41: 250 (1993).
Moore, G. J., *Trends Pharm. Sci.* 15: 124–129 (1994).
Ohlmayer, M. H., et al., *Proc. Natl. Acad. Sci. USA* 90: 23: 10922 (1993).
Olson, G. L., et al., *J. Med. Chem.* 36: 3039–3049 (1994).
Olivera, B. M., et al., *Science* 230: 1338–1343 (1985).
O'Shea, E. K., et al., *Science* 254: 539–544 (1991).
Padmanabhan, S., et al., *Nature* 344: 268–270 (1990).
Pinilla, C., et al., *Biotechniques* 13(6): 901 (1992).
Pinilla, C., et al., *Gene* 128(1): 71 (1993).
Plummer, et al., *Neuron* 2: 1453–1463 (1989).
Rizo, J. and L. M. Gierasch, *Annu. Rev. Biochem.* 61: 387–418 (1992).
Sarin, et al., *Anal. Biochem.* 117: 147–157 (1981).
Scott, J. K. and G. P. Smith, *Science* 249: 386–390 (1990).
Shoemaker, K. R., et al., *Proc. Natl. Acad. Sci. USA* 82: 2349–2352 (1985).
Shoemaker, K. R., et al., *Nature* 326: 563–567 (1987).
Sonnichsen, F. D., et al., *Biochemistry* 31: 8790–8798 (1992).
Wallace, A., et al., *Peptide Res.* 7: 27–31 (1994).
Wiley, R. A. and D. H. Rich, *Med. Res. Rev.* 13: 327–384 (1993).
Zhou, N. E., et al., *J. Biol. Chem.* 267: 2664–2670 (1992).

BACKGROUND OF THE INVENTION

Currently there is widespread interest in using combinatorial libraries of random-sequence oligonucleotides, polypeptides, or synthetic oligomers to search for biologically active compounds (Kramer, et al.; Houghten, et al., 1991, 1992; Houghten, 1994; Ohlmayer, et al.; Dooley, et al., 1993a–1993b; Eichler, et al.; Pinilla, et al., 1993, 1992; Ecker, et al.; and Barbas, et al.). Ligands discovered by screening libraries of this type may be useful in mimicking or blocking natural ligands, or interfering with the naturally occurring interactions of a biological target. They can also provide a starting point for developing related molecules with more desirable properties, e.g., higher binding affinity, greater stability and/or greater bioavailability. In the case of peptide or peptoid combinatorial libraries, such related molecules are termed peptidomimetics.

Considerable effort is being devoted to the rational conversion of information encoded in peptide structures, such as active peptides from a combinatorial library, into peptidomimetics (Farmer, 1980; Wiley and Rich, 1993; Olson, et al., 1994; Rizo and Gierasch, 1992; Hruby, 1993; Moore, 1994). The current paradigm for peptidomimetic design divides the process into three steps (Moore, 1994): (i) identification of the amino acid side chains (pharmacophoric groups) which are responsible for agonist/antagonist activity, (ii) determination of the spatial arrangement of the pharmacophoric groups ("pharmacophore"), and (iii) design of a template upon which these groups can be mounted in a way that retains the spatial orientation of the parent peptide.

While the development of combinatorial peptide libraries (Scott and Smith, 1990; Felici, et al., 1991; Houghten, et al., 1991, Lam, et al., 1991; Geysen and Mason, 1993; Gallop, et al., 1994) has greatly facilitated the accomplishment of the first step, relatively little progress has been made in the second and third steps, that is, the establishment of a conformational model for the pharmacophore and the design of a template upon which these groups can be mounted in a way that retains the spatial orientation of the parent peptide. The present invention provides a means by which such a pharmacophore model may be designed and used for the development and synthesis of conformationally-restricted peptide, peptoid and polypeptide combinatorial libraries.

SUMMARY OF THE INVENTION

In one aspect, the present invention includes a combinatorial library of different-sequence polypeptide members.

Each such member is a coiled-coil dimer "scaffold" formed of two polypeptides (a first and second polypeptide) reversibly bound to one another in an alpha-helical coiled-coil dimer configuration. The coiled-coil dimer scaffold is characterized by (i) an internal region formed by regularly repeating amino acid residues in both polypeptides, and (ii) two exposed regions formed by regularly repeating amino acid residues in the two polypeptides, respectively. The coiled-coil dimer scaffold is stabilized by hydrophobic interactions among the subunits in the internal region of the scaffold. Each member of the library also contains a unique variation of amino acid residues in the exposed region of at least one of the polypeptides.

In one example, the library contains at least $10^3$ members, and amino acid variations occur in at least three different variable residue positions in at least one of the exposed regions corresponding to one of the polypeptides constituting the coiled-coil dimer scaffold.

In various general embodiments, the amino acid variations occur (i) at contiguous residue positions in the exposed region corresponding to at least one polypeptide, (ii) at residue positions in the exposed region of a single α-helical turn in at least one polypeptide, (iii) at residue positions in the exposed regions of two adjacent α-helical turns in at least one polypeptide, or (iv) in a total of at least two different residue positions in the exposed regions of each polypeptide. In another general embodiment, each polypeptide in the library contains at least three helical turns. In still another general embodiment, at least one polypeptide is stabilized in an alpha-helical conformation by a lactam bridge.

In another example, the first and second peptides have different residues at the invariant positions and bind together to form an alpha-helical coiled-coil heterodimer. In a related example, the first and second peptides have identical residues at the invariant positions and bind together to form an alpha-helical coiled-coil homodimer.

In yet another example, the unique variation of amino acid residues in the exposed region is accomplished using representative amino acids that display the basic physicochemical properties associated with naturally occurring amino acids, but exclude many of these naturally occurring amino acids. In other words, the residues used at the variable positions in the peptide sequence are representative amino acids, such as at least one amino acid from each of the groups consisting of (a) Ala, (b) Glu and Asp, (c) Phe, Tyr, and Trp, (d) Gly, (e) Ile and Val, (f) Lys, His, and Arg, (g) Leu, Met, and Cys, (h) Gln and Asn, and (i) Ser and Thr.

In one general embodiment, the first polypeptide contains a terminal bridge segment linking an end of the first polypeptide to an adjacent end of the second polypeptide, the first exposed region further includes this bridge segment and amino acid variations occur in this bridge segment.

In another aspect, the invention includes a combinatorial library of different-sequence polypeptide members. Each member of the library is a polypeptide having N- and C-terminal regions joined by an intermediate, unique-sequence region, where the two terminal regions are bound to one another to form a stable alpha-helical coiled-coil dimer structure, thus constraining movement of the unique-sequence region.

In one general example, the library contains at least $10^3$ members, and amino acid variations occur in at least three different residue positions in the unique-sequence region of the polypeptide. In one general embodiment, the two terminal regions each contain at least three helical turns. In another general embodiment, at least one terminal region is stabilized in an alpha-helical conformation by a lactam bridge. The polypeptide may contain, at the variable positions, representative amino acids such as are described above.

In yet another aspect, the invention includes a combinatorial library of different-sequence peptide members, where each member of the library is an alpha-helical peptide containing a sequence of amino acid residues. The alpha-helical peptide (i) is between 15 and 50 residues in length, (ii) is stabilized by at least one lactam bridge connecting non-adjacent residues, and (iii) has a unique variation of amino acid residues in at least three (variable) positions in the sequence.

In still another aspect, the invention includes a method of identifying a compound capable of interacting specifically with a selected macromolecular ligand. The method includes (a) contacting a library composition, such as any of the compositions mentioned above containing a plurality of different-sequence polypeptide members, with the ligand, and (b) identifying a library member that interacts specifically with the ligand. The members of the library compositions used in this method may have any of the attributes, characteristics or embodiments described for the library compositions above.

In one general embodiment, the macromolecular ligand is a receptor that is known to interact with a polypeptide having at least 20 amino acid residues, and the library members contain amino acid variations in the exposed regions of both polypeptides. In a related embodiment, the selected macromolecular ligand is a substrate capable of enzymatic conversion by an enzyme to a detectable product, and said identifying includes detecting such product.

These and other objects and features of the invention will become more fully apparent when the following detailed description is read in conjunction with the accompanying drawings.

BRIEF DESCRIPTION OF THE FIGURES

FIGS. 2A–E show a schematic representations of adjacent heptads of two scaffold polypeptides in a parallel configuration comparing the stabilizing/destabilizing effects of charged residues at the e and g positions in homodimers vs. heterodimers. FIG. 2A shows a homodimer stabilized by oppositely-charged residues at the e and g positions of a heptad. FIG. 2B shows a heterodimer destabilized by oppositely-charged residues at the e and g positions of a heptad. FIG. 2C shows a homodimer destabilized by positively-charged residues at the e and g positions of a heptad. FIG. 2D shows a heterodimer stabilized by like-charged residues at the e and g positions of a heptad. FIG. 2E shows a homodimer destabilized by negatively-charged residues at the e and g positions of a heptad.

FIG. 9 shows the sequences of LPS epitope peptides used in competitive ELISA assays.

BRIEF DESCRIPTION OF THE SEQUENCES

SEQ ID NO:1 is the amino acid sequence of the EE peptide.

SEQ ID NO:2 is the amino acid sequence of the KK peptide.

SEQ ID NO:3 is the amino acid sequence of the EE terminal repeat.

SEQ ID NO:4 is the amino acid sequence of the EE internal repeat.

SEQ ID NO:5 is the amino acid sequence of the KK terminal repeat.

SEQ ID NO:6 is the amino acid sequence of the KK internal repeat.

SEQ ID NO:7 is the amino acid sequence of peptides KE, 2EK, and Linear 5 (Table 1).

SEQ ID NO:8 is the amino acid sequence of peptides EK, and Linear 7 (Table 1).

SEQ ID NO:9 is the amino acid sequence of peptides 2KE, and Linear 9 (Table 1).

SEQ ID NO:10 is the amino acid sequence of peptide Linear 10 (Table 1).

Figures 3A, 3B:
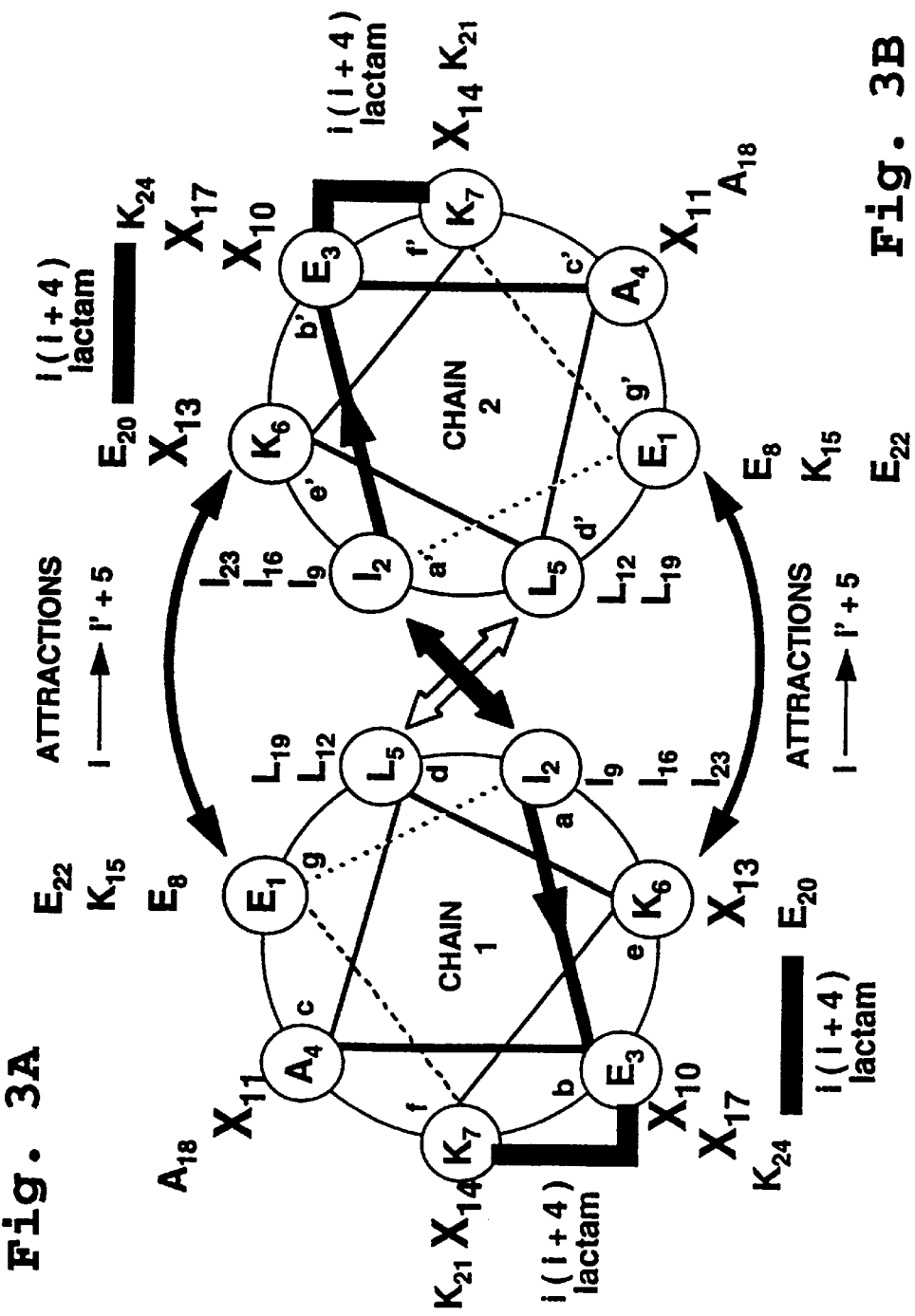
FIG. 3A shows the amino acid sequence (SEQ ID NO:11) and lactam bridge locations of an exemplary generic peptide suitable for use in library compositions of the present invention. Positions at which amino acid residues may be varied to produce a combinatorial library are indicated by $X_i$.
FIG. 3B shows a helical wheel representation of the peptide in FIG. 3A arranged in a parallel α-helical homodimer configuration.

SEQ ID NO:11 is the amino acid sequence of an exemplary generic library peptide (FIG. 3A).

Figures 5A, 5B:
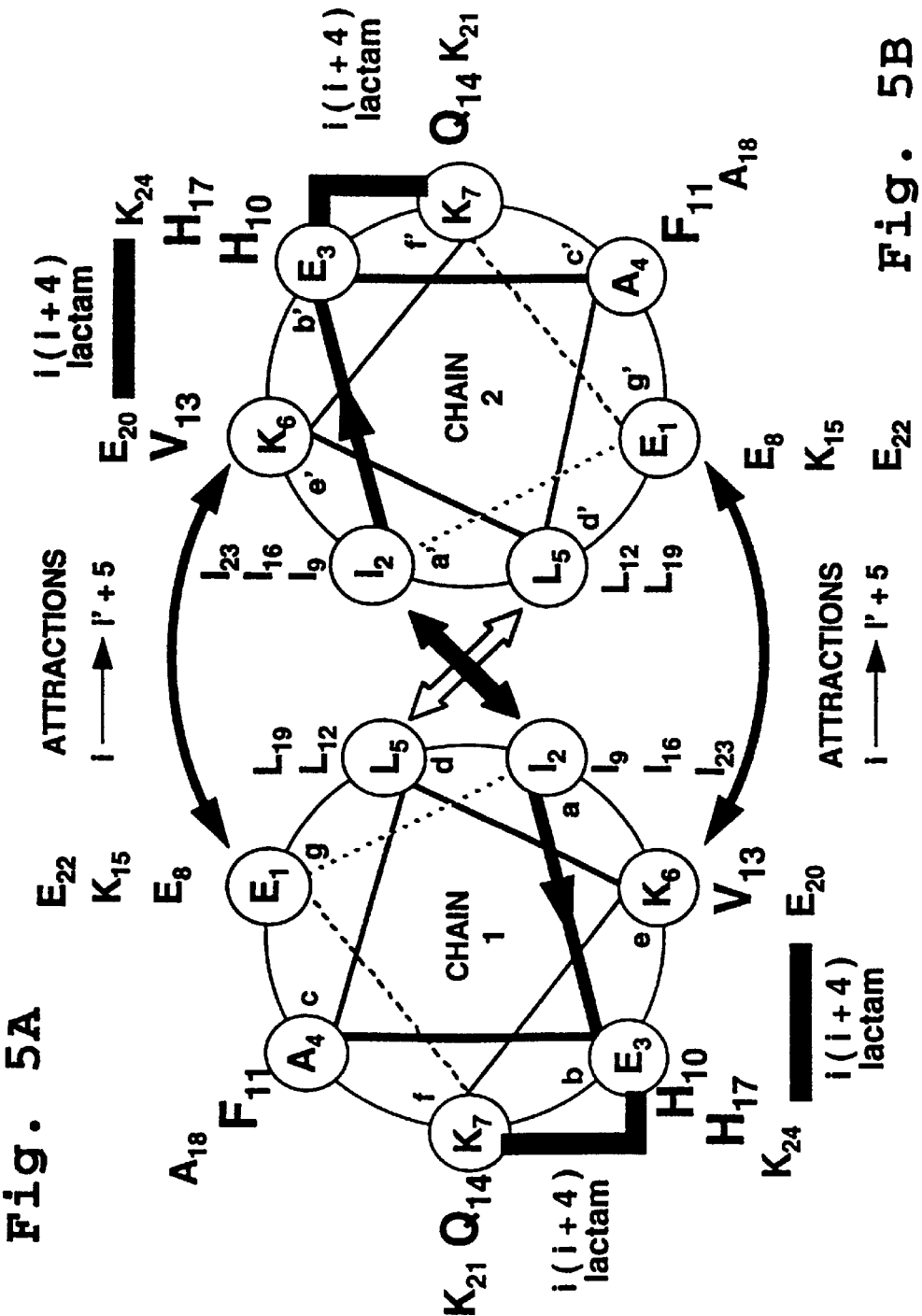
FIG. 5A shows the amino acid sequence (SEQ ID NO:12) and lactam bridge locations of the LPS epitope peptide.
FIG. 5B shows a helical wheel representation of the peptide in FIG. 5A arranged in a parallel α-helical homodimer configuration.

SEQ ID NO:12 is the amino acid sequence of the LPS epitope library peptide (FIG. 5A).

SEQ ID NO:13 is the amino acid sequence of the single-stranded peptide shown in FIG. 9.

SEQ ID NO:14 is the amino acid sequence of the linear ZnF peptide shown in FIG. 9.

SEQ ID NO:15 is the amino acid sequence of the CP1 peptide (Kim and Berg, 1993).

DETAILED DESCRIPTION OF THE INVENTION

I. Definitions

The term "peptide" designates a chain of amino acid based polyamides. The chain can vary in length anywhere from 2 amino acids to approximately 50 amino acids.

The term "polypeptide" also designates a chain of amino acid based polyamides. The chain can vary in length anywhere from 2 amino acids to 100 or more amino acids. Chains longer than approximately 100 amino acids are typically termed "proteins".

Unless otherwise indicated, the sequence for peptides and polypeptides is given in the order from the amino terminus to the carboxyl terminus.

The term "benign medium" as used herein, describes a physiologically-compatible aqueous solution typically having a pH of between about 6 and about 8 and a salt concentration of between about 50 mM and about 500 mM. Preferably, the salt concentration is between about 100 mM and about 200 mM. An exemplary benign medium, designated as buffer A, has the following composition: 50 mM potassium phosphate, 100 mM KCl, pH 7. Equally effective benign media may be made by substituting, for example, sodium phosphate for potassium phosphate and/or NaCl for KCl.

II. General Overview of the Invention

The present invention relates to combinatorial peptide, peptoid or polypeptide libraries, where the variable residues or sequences that underlie the sequence variability among the different members of the library are presented or contained on a conformationally-restricted, or semi-rigid, scaffold. This combination of sequence variability and structural consistency among the members of the library facilitates the development of peptidomimetics based on individual members of the library that have a high affinity for a selected macromolecular ligand, since the basic structure of the library members is known.

According to the teachings of the present invention, an exemplary scaffold structure suitable for a structurally-consistent presentation of various sequence combinations to a selected ligand is a stabilized α-helix. The helix is comprised of a peptide or polypeptide whose sequence contains "invariant" positions, where the same amino acid residues are incorporated in each member of a particular library, and "variable" positions, at which the amino acid residues are varied among the different members of the library to achieve the library's diversity.

The invariant positions are important for maintaining or stabilizing the peptide in an α-helical conformation. Such stabilization is an important aspect of the invention, since many residues which may be employed at the variable positions may have a destabilizing effect on the α-helical conformation. Several strategies may be used to stabilize the scaffold peptides into an α-helix. One is through the use of covalent bonds, such as lactam bridges, to link residues in a manner that makes an α-helix a very stable and energetically-favorable conformation, even in instances where the peptide contains residues that would destabilize an unconstrained α-helix. The residues that are typically employed in the formation of lactam bridges are Glu and Lys residues, at a spacing of (i, i+4), in the direction Glu to Lys. Accordingly, peptides stabilized by lactam bridge(s) preferably contain these residues at "invariant" positions dictated by the location of the lactam bridge(s).

Another means of stabilizing an α-helical conformation is through the formation of α-helical coiled-coil dimers, also referred to as coiled-coil dimer scaffolds. A coiled-coil dimer scaffold constitutes a molecule whose basic structure remains relatively constant among the different members of the combinatorial library, despite variations at the variable residue positions. Coiled-coil dimer scaffolds are stabilized primarily by hydrophobic interaction among hydrophobic residues, such as Ile, Leu or Val, at the region of contact between the peptides, though other residues may play a significant role in the dimer stabilization/destabilization, as is discussed below.

Of course, the above exemplary stabilization approaches may be combined, such that a library contains coiled-coil dimer scaffolds, each comprised of two polypeptides, one or both of which in turn are stabilized by lactam bridges. It will also be appreciated that while lactam bridges and coiled-coil formation are exemplary stabilization means for α-helical members of a combinatorial library, other stabilization means effective to stabilize α-helices having variable positions are also considered to be within the scope of the present invention.

The two polypeptides constituting a coiled-coil dimer scaffold are sometimes referred to as scaffold polypeptides. The scaffold polypeptides typically contain between about 15 and about 50 residues. In discussions relating to coiled-coil dimer formation, they are sometimes referred to herein as SP1 (scaffold polypeptide 1), and SP2 (scaffold polypeptide 2). The polypeptides SP1 and SP2 may have the same set of residues, or different sets of residues, at their "invariant" positions, depending on whether it is desired to form heterodimers or homodimers, as is described in detail below. Dimers of SP1 and SP2 are sometimes designated herein as SP1~SP2. If SP1 and SP2 have the same amino acid residues at their respective invariant amino acid positions, the resulting coiled-coil dimer scaffold is said to be a "homodimer", even though the two peptides which constitute the scaffold may have different amino acid residues at their variable positions. If SP1 and SP2 have different amino acid residues at their respective invariant amino acid positions, the resulting coiled-coil dimer scaffold is said to be a "heterodimer". Conditions favoring either heterodimer or homodimer formation are discussed in detail below.

Peptides in an α-helical coiled-coil conformation reversibly bind to one another in a characteristic manner that is determined by the identity of the residues at the invariant positions of each peptide. The tertiary structure of an α-helix is such that 7 amino acid residues in the primary sequence correspond to approximately 2 turns of the α-helix. Accordingly, a primary amino acid sequence giving rise to an α-helical conformation may be broken down into units of 7 residues each, termed heptads. The scaffold polypeptides are comprised of a series of heptads in tandem. When the sequence of a heptad is repeated in a particular scaffold polypeptide, the heptad may be referred to as a "heptad repeat", or simply "repeat". The heptad repeats give rise to regularly repeating heptad positions, corresponding to regularly-repeating amino acid residues, along the α-helix.

In the context of the α-helices SP1 and SP2 interacting in a coiled-coil fashion, the individual positions of the heptads in each polypeptide are identified by letters (a–g). As is discussed below, the helices contact each other along the faces defined by the a and d positions in each helix. This contact region comprises the "internal" region of a coiled-coil dimer scaffold and is formed by regularly repeating amino acid residues (i.e., the residues at heptad positions a and d), which are typically hydrophobic residues and are generally "invariant" in combinatorial polypeptide compositions designed to form coiled-coil dimer scaffolds.

The remaining heptad positions in each of the scaffold polypeptides (i.e., positions b,c,e,f and g) are considered "external", or "exposed", since they are at the outward-facing aspects of a coiled-coil dimer scaffold, and are in contact with the solvent in which the coiled-coil dimer scaffold is suspended. Accordingly, the regularly-repeating amino acid residues at these positions in each of the two polypeptides constitute the exposed regions of a coiled-coil dimer scaffold, where the two exposed regions of the coiled-coil dimer correspond to the exposed positions of the two polypeptides, respectively. Each of the external, or exposed positions may be either variable or invariant, depending on the stabilization strategy selected. Further, a particular external position, such as b, may be variable in one heptad of a polypeptide and invariant in another heptad of the same polypeptide, again, depending on the stabilization strategy and on the desired spatial arrangement of the variable residues when the polypeptide containing them adopts a stabilized α-helical or coiled-coil conformation.

Amino acid variations at the variable positions in the exposed region of the scaffold give rise to different-sequence polypeptide members of a combinatorial polypeptide library. Depending on the number of variable positions and on the number of different residues which can occupy each variable position, such a library can have over $10^3$ different-sequence members. For example, a combinatorial peptide library where each peptide has three variable positions, each of which can contain any of 19 different amino acid residues, has $19^3$, or 6859 different-sequence members.

Combinatorial libraries which employ a coiled-coil dimer scaffold may contain either homodimer scaffolds or heterodimer scaffolds. Homodimer libraries are somewhat easier to synthesize, since only one peptide pool needs to be made. Heterodimer libraries may be constructed with one of the scaffold polypeptides (e.g., SP1) being a "combinatorial" polypeptide, in that it contains variable residues, and the other scaffold polypeptide (SP2) being a "stabilizing" polypeptide, in that all of the positions in the sequence are "invariant", and the sequence of the polypeptide is optimized for maximal stabilization of coiled-coil SP1~SP2 dimers.

SP1 and SP2 can be connected by a bridge segment, which is exposed to the solution, and can contain variable positions in its sequence. Such a bridge segment can be synthesized with one or both scaffold polypeptides (e.g., the two polypeptides and the bridge segment can be synthesized as one continuous polypeptide), or it may be attached chemically subsequent to synthesis to connect the termini of SP1 and SP2 to one another. A bridge segment attached to the polypeptides as above is conformationally restrained by the formation of an SP1~SP2 coiled-coil dimer. If SP1, SP2 and the bridge segment are a single polypeptide, the polypeptide can be considered to have an N-terminal region corresponding to one scaffold polypeptide (e.g., SP1), a C-terminal region corresponding to the other scaffold polypeptide (SP2), and an intermediate, unique-sequence region, corresponding to a bridge segment containing variable positions suitable generating the diversity of a combinatorial library. The two terminal regions (i.e., SP1 and SP2) are bound to one another to form a stable alpha-helical coiled-coil dimer structure, constraining movement of the unique-sequence region (bridge segment).

Any of the combinatorial libraries described above may be used in a screen to identify a unique member of that library (i.e., a specific compound) that is capable of interacting specifically with a selected macromolecular ligand. Examples of suitable macromolecular ligands include antibodies, antibody fragments, receptors, ion channels, enzymes, enzyme substrates, and the like. Such ligands may bind to unique members of the library in a number of ways. For example, the ligand can be a specific substrate whose breakdown products can be detected, and the library screen can involve detection of such breakdown products by a unique member of the library that has the capacity to break down the substrate. In the case of ionotrophic receptors, such as ion channels, the ligand can be the pore of an ion channel and the screen can involve detection of block of ionic current through the channel by a unique member of the library. Alternatively, the ligand may be an agonist, antagonist, or toxin binding site on a receptor or ion channel and the screen can involve monitoring of ionic current through the channel (in the case of ionotrophic receptors), or high-affinity binding to the channel or receptor protein. If the ligand is an antibody or antibody fragment, the screen can involve detection of immunocomplexes formed between a member of the library that contains an epitope recognized by the antibody, and the antibody or antibody fragment.

In all cases, the screens outlined above involve contacting a library composition, such as is described above, with the ligand, and identifying a library member that interacts specifically with the ligand. The member may be identified, for example, by using a positional scanning format (Pinilla, et al., 1992; Wallace, et al., 1994). In this approach, exemplified here for a peptide with five variable positions, five different sets of sublibraries are prepared. The variable positions in the sets of sublibraries take the form $O_1X_2X_3X_4X_5$, $X_1O_2X_3X_4X_5$, $X_1X_2O_3X_4X_5$, $X_1X_2X_3O_4X_5$, $X_1X_2X_3X_4O_5$. The sublibraries in a particular set each contain a different known residue at one of the variable positions ($O_i$), and all the possible combinations of residues at the remaining variable positions ($X_i$). By screening all of the libraries in all five sets, a subset of "high affinity" amino acid residues can be identified for each variable position. This restricted subset can then be used to generate additional sets of libraries, which can be used to identify specific high-affinity members, or compounds, which bind to the selected macromolecular ligand. Variations which can speed up and simplify this identification process are detailed below.

III. Coiled-Coil Stabilization-Features of Scaffold Polypeptides

The two scaffold polypeptides (SP1 and SP2) useful for coiled-coil stabilization of α-helical combinatorial peptide or peptoid libraries are of similar, if not identical size, each ranging from about 15 to about 50 residues (2 to 7 heptads) in length. The specific exemplary scaffold polypeptides described herein range from about 20 to about 30 residues in length. SP1 and SP2 may be formed of two separate polypeptide chains, or, alternatively, may be formed of a single polypeptide chain wherein the two scaffold polypeptides are linked by a bridge segment that does not substantially interfere with the association of SP1 and SP2 into a coiled-coil heterodimer.

The peptides may be synthesized by a variety of methods known to those skilled in the art. For example, an ABI Model 430A peptide synthesizer may be used with conventional t-Boc chemistry as described previously by Hodges, et al., (1988). Alternatively, they may be synthesized using a Labortec SP 640 peptide synthesizer as detailed in Example 1.

Subsequent to synthesis, the peptides are purified by any of a number of methods known to those skilled in the art, for example using reversed-phase high performance liquid chromatography (RPC) and a "SYNCHROPAK" RP-4 column, as detailed in Example 1.

The composition and purity of the peptides can be verified by several methods, including amino acid composition mass analysis on a Beckman model 6300 amino acid analyzer and molecular weight analysis using time of flight mass spectroscopy on a "BIOION-20" Nordic, as detailed in Example 1.

A. Coiled-Coil Formation

Figure 1A:
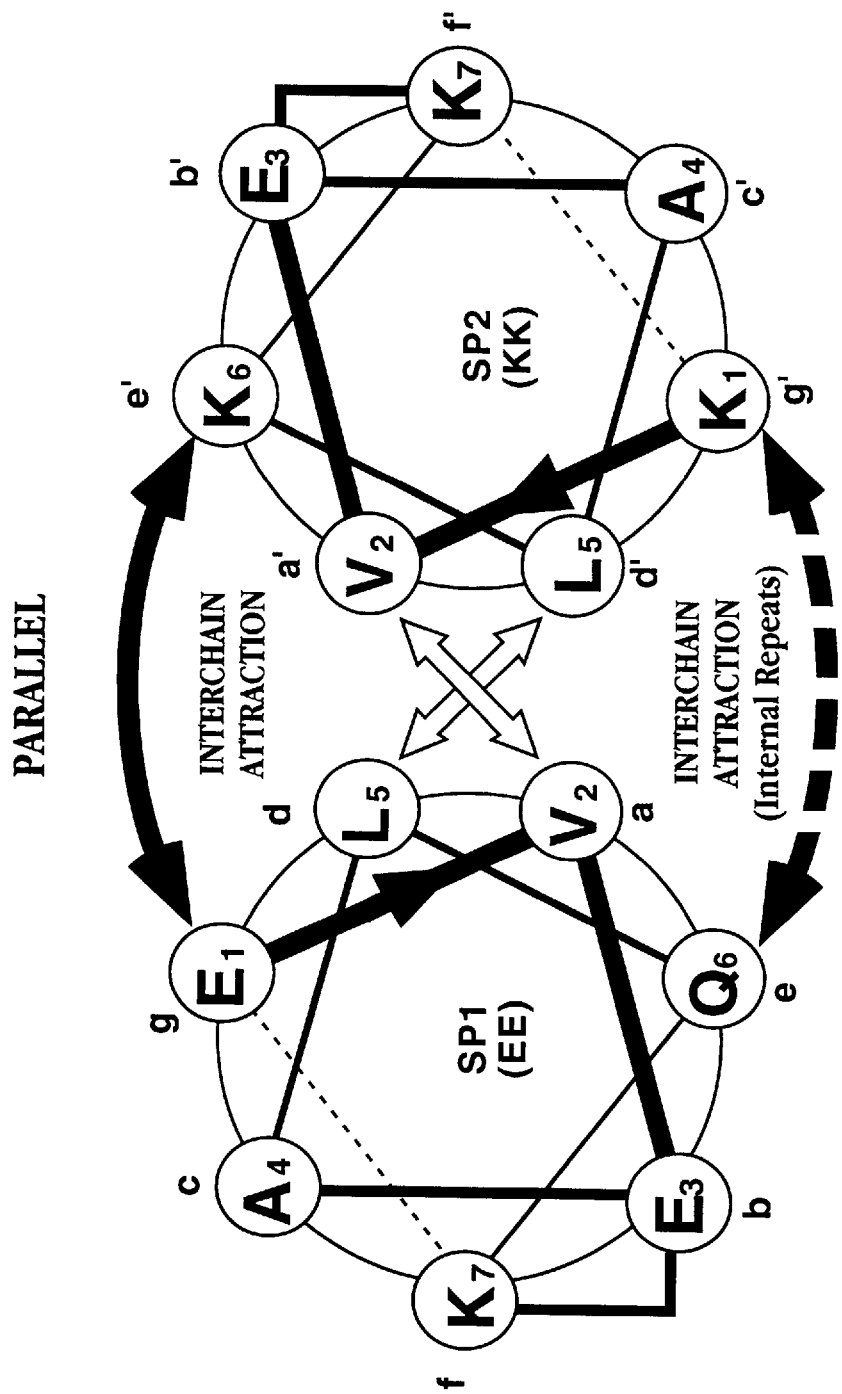
FIG. 1A shows helical wheel representations of terminal heptads of two exemplary scaffold polypeptides in a parallel α-helical heterodimer configuration.
Figure 1B:
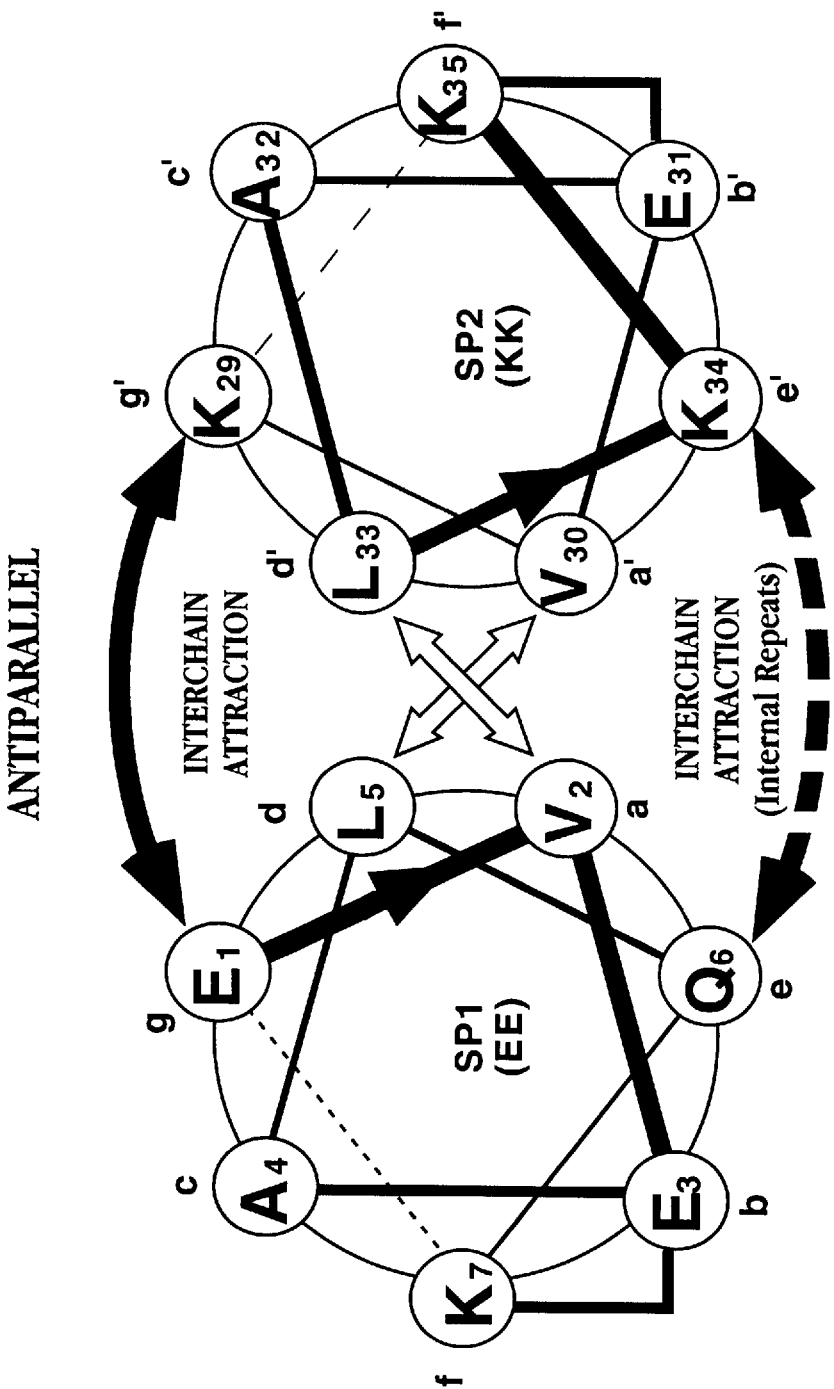
FIG. 1B shows helical wheel representations of terminal heptads of two exemplary scaffold polypeptides in an antiparallel α-helical heterodimer configuration.

The dimerization of SP1 and SP2 occurs due to the presence of a repeated heptad motif of conserved amino acid residues. The individual positions in each heptad are designated by the letters a through g for SP1, and a' through g' for SP2, as shown in FIGS. 1A and 1B. The positions (e.g., a', g') of SP2 are sometimes referred to without the (') symbol in general discussions of heptad positions in scaffold polypeptides, below.

An appropriate heptad motif, or repeat, directs the SP1 and SP2 polypeptides to assemble into a dimeric α-helical coiled-coil structure under permissible conditions (see below). The individual α-helical peptides contact one another along their respective hydrophobic, or internal faces, defined as the a and d positions of each heptad.

SP1 and SP2 may assemble into a dimer coiled-coil helix (coiled-coil heterodimer) in either parallel or antiparallel configurations. In a parallel configuration, the two scaffold polypeptide helixes are aligned such that they have the same orientation (amino-terminal to carboxyl-terminal). In an antiparallel configuration, the helixes are arranged such that the amino-terminal end of one helix is aligned with the carboxyl-terminal end of the other helix, and vice versa.

Diagrams of the relative orientations of the a–g positions of two interacting α-helices are shown in FIGS. 1A and 1B. FIG. 1A shows an end-on schematic of the first two turns (one heptad) of two exemplary scaffold polypeptides, EE and KK (SEQ ID NO:1 and SEQ ID NO:2) arranged in a parallel configuration. FIG. 1B shows an end-on schematic of the same scaffold polypeptides arranged in an antiparallel configuration.

In FIGS. 1A and 1B, amino acids are circled and indicated by the one-letter code, and consecutive amino acid positions are numbered and joined by lines with arrow heads indicating the N-terminal to C-terminal direction. Interactions between the two helixes are indicated by arrows. Wide arrows crossing between the helixes depict hydrophobic interactions between the a and d positions of adjacent helixes.

Ionic interactions between the e and g positions of adjacent helixes are indicated as curving arrows above and below the nexus of the helixes. Position e of peptide EE (SEQ ID NO:1) is a Gln in the first and last heptad, and a Glu in the internal heptads. The (bottom) curving arrow depicting ionic interactions with this position is drawn with a dashed line to indicate that ionic interactions are present between internal heptads of the helixes, but not between the first and last, or terminal, heptads.

Lactam bridges are indicated as a right-angle line between the f and b positions within each helix.

B. Hydrophobic Interactions in Coiled-Coil Stability

The hydrophobic interactions between the helixes are due to hydrophobic residues at the a and d positions of the scaffold polypeptides. Residues at these positions, effective to maintain the helixes in contact, include leucine, isoleucine, valine, phenylalanine, methionine, tryptophan, tyrosine, and derivatives of any of the above. Depending on the length of SP1 and SP2, other residues, including alanine, cysteine, serine, threonine, asparagine and glutamine may also occupy a or d positions in some heptads, so long as others are occupied by hydrophobic residues.

Appropriate selection of the specific residues to occupy the a and d positions is an important aspect of the present invention. If the hydrophobic interactions are strong, as is the case, for example, between helixes containing Ile at one of the positions and Leu at the other position, a significant fraction of the helixes will form as homodimers at pH 7, even if like-charged residues are present at the e and g positions to discourage homodimer formation (see part C., below). This interaction is exploited in the construction of an exemplary peptide suitable for the construction of combinatorial homodimer libraries, and is discussed in detail with reference to FIGS. 3B and 5B, below.

If, on the other hand, residues at the a and d positions are selected such that the hydrophobic interactions are too weak (for example, Ala at both positions), the helixes may not form coiled-coil dimers at all (see "Single Stranded" peptide in FIG. 9; SEQ ID NO:13). If heterodimer formation is desired, residue pairs are preferably selected that promote the formation ≧95% heterodimers at pH 7. The degree of heterodimer vs. homodimer formation may be measured as described, for instance, in Example 3. An exemplary pair of residues at the a and d positions, that results in hydrophobic interactions conducive to ≧95% heterodimer formation at pH 7, comprises Leu at one of the positions and Val at the other position. These residues are present at the a and d positions of scaffold polypeptides EE (SEQ ID NO:1) and KK (SEQ ID NO:2).

C. Ionic Interactions in Coiled-coil Stability

Dimeric coiled-coil conformations of α-helixes can be stabilized by ionic interactions between residues at the e and g positions of adjacent helixes, as is illustrated in FIGS. 2A–E. If each helix of a dimer has a positively-charged residue at one position, for example, e, and a negatively-charged residue at the other position, for example, g, homodimer formation is favored (FIG. 2A; compare with heterodimer in FIG. 2B). However, if each helix has like-charged residues at both positions, then two oppositely-charged helixes will tend to associate into heterodimers (FIG. 2D), as opposed to forming homodimers (FIG. 2C, 2E).

The conformation of polypeptides, such as SP1 and SP2, in solution can be determined from CD spectra of the solution. These data provide information as to the conformation of the individual peptides themselves (random coil vs. α-helical), as well information as to the relative amounts of heterodimer vs. homodimer complexes of SP1 and SP2. Example 2 details one method of measuring CD spectra. Example 3 details how a CD spectra measurements can be used to assess the conformation of peptides in solution.

In the diagram shown in FIG. 2, ionic interactions between the two helixes arise from negatively-charged (Glu) residues at the e and g positions on SP1 (EE; SEQ ID NO:1), and positively-charged (Lys) residues at the e and g positions on SP2 (KK; SEQ ID NO:2). However, the terminal heptads of peptide EE (SEQ ID NO:1) have uncharged residues (Gln) at the e position, as opposed to the charged Glu at that position in internal repeats. Accordingly, ionic interactions involving the e position of EE will occur at internal (SEQ ID NO:4), and not terminal (SEQ ID NO:3), repeats.

Negatively-charged residues can be aspartic acid, glutamic acid or derivatives thereof. Positively-charged residues can be lysine, arginine, histidine, or derivatives thereof.

Ionic interactions between other positions in a heptad may also exert significant influences on helix stability. For example, position e in EE peptide (SEQ ID NO:1) terminal repeats is a Gln, as opposed to a Glu, because Glu residues at both positions would tend to destabilize an α-helical conformation through ionic repulsions (see FIGS. 1A and 1B). Many of the destabilizing effects, however, may be overcome by introducing stabilizing covalent modifications, such as lactam bridges (discussed below in part E).

D. Conditions Favorable for Coiled-coil Formation

Scaffold polypeptides comprised of repeating heptads and designed according to the guidance presented in parts A through C, above, will readily form coiled-coil dimers in a benign medium, defined above in part I. The degree of α-helical coiled-coil heterodimer formation can be determined from CD spectra, as described, for instance, in Example 3.

Coiled-coil dimers may form under conditions outside the pH and salt range given for a benign medium, but some of the molecular interactions and relative stability of heterodimers vs. homodimers may differ from characteristics detailed above. For example, ionic interactions between the e and g positions that tend to stabilize heterodimers may break down at low or high pH values due to the protonation of, for example, Glu side chains at acidic pH, or the deprotonation of, for example, Lys side chains at basic pH.

Aforementioned effects of low and high pH values on coiled-coil heterodimer formation may be overcome by increasing the salt concentration, which can neutralize the stabilizing ionic attractions or suppress the destabilizing ionic repulsions. Certain salts have greater efficacy at neutralizing the ionic interactions. For example, in the case of the KK peptide (SEQ ID NO:2), a 1M or greater concentration of $ClO_4^-$ anions is required induce maximal α-helical structure (as determined by CD measurements performed as detailed in Example 2), whereas a 3M or greater concentration of $Cl^-$ ions is required for the same effect. The effects of high salt on coiled-coil formation at low and high pH also show that interhelical ionic attractions are not essential for helix formation, but rather, control whether a coiled-coil tends to form as a heterodimer vs. a homodimer.

E. Heptad Variation in Scaffold Polypeptides.

Parts A, B and C, above, present guidelines as to which amino acid residues may be included, and which amino acid residues are preferable, at specific (e.g., invariant) positions in heptads of scaffold polypeptides that will typically result in those peptides forming α-helical coiled-coil structures in a benign medium. This part describes some examples of how heptads with sequences which are in compliance with the guidelines presented in parts A through C, above, can be arranged within the scaffold polypeptides.

Scaffold polypeptides of the present invention may each contain from two to a plurality (e.g., 7) of heptads (i.e., four to a plurality, e.g., 14, helical turns). The specific residues at the invariant positions of each of those heptads may all be the same, or they may differ. In particular, the residues at the invariant positions of the first and last heptads, or terminal repeats, may differ from the residues at the invariant positions of the interior or intermediate heptads or repeats. Furthermore, the residues at the invariant positions of the internal repeats may differ from one another depending on, for example, the selected location of variable residues. For example, the terminal repeats of both the EE and KK peptides incorporate residues designed to form lactam bridges to stabilize an α-helical conformation.

As is detailed below, positions which are invariant in some heptad(s) of a peptide may be considered variable in other heptad(s) of the same peptide. Similarly, because the salient interactions between two scaffold polypeptides in an α-helical coiled-coil heterodimer pair are between adjacent, "complementary" heptads in each peptide, the primary sequence of invariant residues in heptads within a scaffold polypeptide can vary, so long as the invariant residues within each heptad interact favorably with invariant residues in the complimentary heptad of the second scaffold polypeptide.

F. Covalent Modification of Scaffold Polypeptides

The scaffold polypeptide sequences may include residues designed to further stabilize the α-helical conformation of each scaffold polypeptide in a coiled-coil dimer. For example, peptides EE and KK have glutamic acid and lysine residues at the b and f positions, respectively, of the terminal repeats. These residues can react under the appropriate conditions, detailed in Example 4, to form a lactam bridge, as schematized in FIG. 1. The value of such bridges is discussed below, in relation to Example 5.

IV. Positioning of Variable Residues

The positions of variable residues in scaffold polypeptides comprising a library of the present invention depends on the nature of the scaffold and the type of stabilization strategy employed. In all cases, however, the variable positions are exposed to the solvent when the scaffold peptide is in solution. For example, in the case of a library comprised of coiled-coil dimers, the amino acid variations occur at the exposed regions of a dimer (i.e., at positions e, b, f, c or g of an α-helix heptad). This can appreciated from a helical wheel representation of a coiled-coil dimer, such as is shown in FIG. 1A. The positions of amino acid variation are termed "variable" residues, while the remaining positions are termed "invariant" residues.

An exemplary peptide useful in the construction of a library comprised of coiled-coil dimers is shown in FIG. 3A. The peptide sequence (SEQ ID NO:11) contains five positions at which the amino acid residues vary from one library member to the next, and forms approximately three and a half turns in an α-helical conformation. The positions are identified in FIG. 3A as $X_1$, $X_2$, $X_3$, $X_4$ and $X_5$, and are located at positions 10, 11, 13, 14 and 17, respectively, in the peptide sequence. Note that the variable position number (i in $X_i$) does not necessarily correspond to the position of the residue in the peptide sequence. The peptide also contains two lactam bridges, indicated by lines under the sequence, between Glu and Lys residues. FIG. 3B shows a helical wheel representation of a coiled-coil homodimer formed by association of two peptides having the sequence in FIG. 3A (SEQ ID NO:11). The representation is similar to that illustrated in FIG. 1A, except that the entire sequence, as opposed to only the first coil, is represented. The relative positions of the residues, as well as locations of lactam bridges, are indicated. Also indicated are hydrophobic interactions between the a and d positions of the a helixes, and stabilizing ionic interactions between the e and g positions. As can be appreciated from FIG. 3B, the variable amino acid positions ($X_1$, $X_2$, $X_3$, $X_4$ and $X_5$,) are all located on exposed portions of the coiled-coil dimer.

Figure 4:
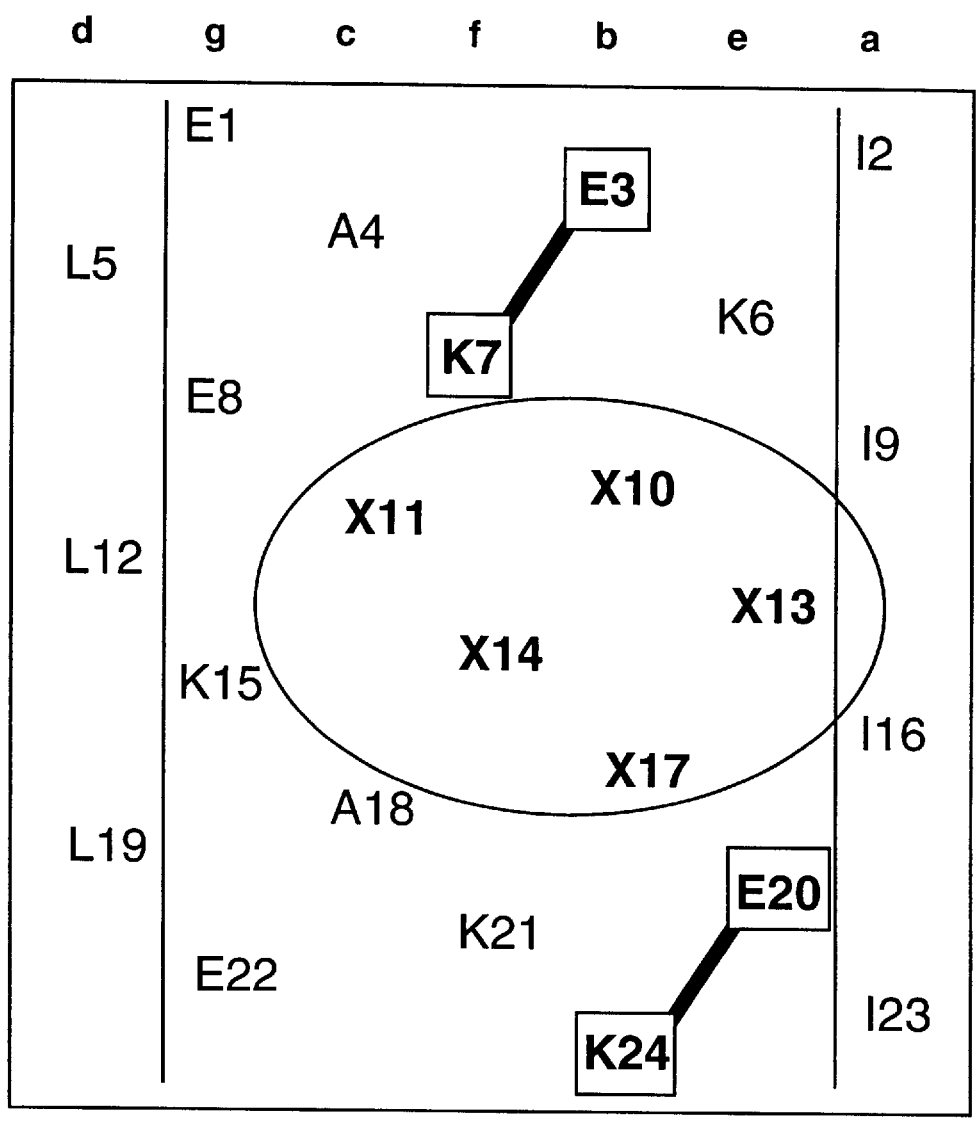
FIG. 4 shows a helical net representation of an α-helix formed of the peptide shown in FIG. 3A (SEQ ID NO:11).

FIG. 4 shows a helical net representation of an α-helix predicted from the sequence shown in FIG. 3A (SEQ ID NO:11). A helical net is a side view of the α-helix if it were cut lengthwise and laid flat, and is useful for visualizing the 2-dimensional spatial arrangement of particular residues in an α-helix. The heptad positions are indicated along the top of the figure. The exposed portion of the helix (if the helix were paired with another one in a coiled-coil dimer) is between the two vertical lines separating heptad positions d and a, respectively, from the rest of the heptad positions in the figure.

It can be appreciated from FIG. 4 that the five variable positions ($X_1$, $X_2$, $X_3$, $X_4$ and $X_5$,) are arranged such that they form a cluster when the peptide assembles into an α-helix, or is paired with another α-helix in a coiled-coil configuration. The variable positions can occur in a number of other configurations as well. For example, with respect to coiled-coil dimer scaffolds, they can occur at contiguous residue positions, and can occur in the exposed region of the dimer scaffold corresponding to one polypeptide (e.g., SP1), but not necessarily on the other polypeptide (SP2). They can also all occur within a single α-helical turn, a single heptad (two helical turns; e.g., see positions of $X_1$, $X_2$, $X_3$, $X_4$ in FIGS. 3B and 4), or in more than two helical turns. In other embodiments of the invention, variable positions can be located in both polypeptides of a coiled-coil dimer, enabling a particular combinatorial dimer to bind to, for example, a receptor with two or more spatially-distinct but related binding sites.

All naturally-occurring amino acids, with the exception of proline, as well as many synthetic amino acids, may be incorporated at the variable positions. The amino acids may include standard and non-standard and derivatized L- and D-amino acids, amino acids coupled through non-amide linkages (forming a polypeptoid), and the like. Non-natural amino acids include, but are not limited to, 2-aminobutyric acid (Abu), cyclohexylalanine (Cha), norleucine (Nle), norvaline (Nva), ornithine (Orn), homophenylalanine (Hph), 4-chlorophenylalanine (Fcl), 4-nitrophenylalanine (Fno) and phenylglycine (Phg).

The remaining residues are preferably selected to promote stabilization of the α-helix and or coiled-coil dimers, as discussed above. For example, lactam bridges may be incorporated at the ends of the α-helix for stabilization. For coiled-coil dimer scaffolds, hydrophobic residues are placed at the a and d positions and charged residues selected for stabilizing homodimers or heterodimers may be placed at the e and g positions.

V. Stabilization of α-Helical Peptides by Lactam Bridges

The peptide or polypeptide members of combinatorial libraries of the present invention are stabilized such that the resulting combinatorial library is conformationally-homogeneous. One method of achieving stabilization effective to result in a conformationally-homogeneous library, particularly in cases where the peptides have a sequence that allows them to adopt an α-helical conformation, is to incorporate lactam bridges (between Lys and Glu residues) into the individual peptides, as described above.

Experiments performed in support of the present invention and detailed in Example 5, below, demonstrate the stabilization of α-helixes that may be achieved by selective incorporation of such lactam bridges. For example, the data show that there was a significant difference in helical content going from an (i, i+3) to an (i, i+4) lactam bridge. Although both should lie on the same face of the helix, (i, i+3) lactams were not as effective in stabilizing helical content in the exemplary library peptides as were (i, i+4) lactams.

The helical content of scaffold polypeptides was also found to depend on the orientation of the (i, i+4) lactam bond. Lactam bridges oriented Lys to Glu were typically less helical than their linear homologs. On the other hand, Glu to Lys lactams were more helical than their linear counterparts and are considered preferable in the methods and compositions of the present invention.

Though not wishing to be bound by any particular mechanism, it is contemplated that this orientational effect may be due to the differences in length of the Glu and Lys side-chains, resulting in the carbonyl groups of the lactam bridges being in different environments when the orientation is reversed. Modeling studies performed in support of the present invention suggest that for KE lactams, the proximity of the carbonyl oxygen of the lactam bond falls within the Van der Waals contact distance of the carbonyl oxygen of the $i^{th}$ peptide bond (Lys-Ala), and that the random structure found in benign conditions alleviates this disruptive interaction.

The results presented in Example 5 and summarized above demonstrate the effects of lactam position and orientation in inducing and stabilizing helical content of peptides, and support the value of lactams bridges as a method of stabilizing an α-helical conformation in peptide members of a conformationally-restricted combinatorial library.

VI. Subunit Composition of Combinatorial Libraries

Combinatorial libraries of the present invention may be composed of homodimers, heterodimers, or monomers. The term "homodimer", when applied to a member of combinatorial library composition of the present invention, is understood to mean a dimer comprised of peptides having the same residues at the invariant positions in the sequence, even though they may have different residues at the variable positions. For example, a library comprised of dimers of peptides having the general form of the peptide shown in FIGS. 3A, 3B and 4, would be considered to be a library of "homodimers". Homodimer libraries involve a simpler synthesis strategy, since only one pool of peptides needs to be carried through the synthesis.

The term "heterodimer", when applied to a member of a combinatorial library, is understood to mean a dimer comprised of two peptides, each from a different class. Peptides from one class may have one set of residues at the invariant positions, and peptides from the other class may a different set of residues at the invariant positions. The strategies discussed above identifying conditions conducive to homodimer formation vs heterodimer formation, and vice versa (e.g., ionic interactions between e and g positions), may be applied in the design of peptides used in the construction of libraries of the present invention. In particular, classes of peptides with the appropriate invariant residues may be prepared, such that upon mixing, heterodimers between peptides of the two classes are preferentially formed. Such an approach may be useful, for example, in cases where a receptor is known to have two spatially-distinct binding sites, each of which have different known characteristics. Two pools, or classes of combinatorial peptides may be prepared, where the locations and identities of specific residues employed in each pool for incorporation at the variable positions are selected to be compatible with the characteristics of one of the two sites. This may involve, for example, differences in the locations of the variable residues between the two α-helixes, or differences in the general types of amino acids used at the variable positions in the two pools.

Heterodimer libraries may also be employed in a configuration where only one of the scaffold peptides forming a library dimer has variable residues, and the other scaffold peptide serves only as a structural stabilizer. In this approach, the "stabilizing" peptide may be designed to contain a sequence of amino acids optimized for maximizing the stability of a coiled-coil heterodimer scaffold.

In addition to the coiled-coil dimer libraries discussed above, the present invention also includes combinatorial libraries containing α-helical peptide monomers with regions of amino acid residue variation. The monomers may be stabilized in the α-helical conformation using, e.g., lactam bridges. In contrast to peptides designed to form coiled-coils, peptides designed for α-helical monomer libraries typically do not use hydrophobic residues such as Ile, Leu and Val at positions a and d of the α-helix heptad. Rather, they employ residues with smaller, less hydrophobic side chains, such as Ala (see FIG. 9, SEQ ID NO:13). Similarly, peptides for use in monomer libraries do not necessarily benefit from charged residues at positions e and g. An exemplary α-helical peptide suitable as a model for a monomeric α-helical combinatorial library is presented and discussed below.

VII. Synthesis of Libraries

Combinatorial libraries of the type useful in the present invention may be formed by a variety of solution-phase or solid-phase methods, in which subunits are added stepwise to growing oligomers. Since the peptides comprising libraries of the present invention typically contain invariant residues at their termini, all of the peptides in a particular library pool typically begin their synthesis as a single batch, with a unique amino acid residue added at each coupling step at an invariant position. When the synthesis reaches the point where the next residue to be added is at a variable position, a mixture of amino acids, containing the amino acids desired at that variable position, is added to the synthesis mixture (Houghten, et al., 1991). The synthesis is carried out until the desired peptide, having the desired variation at selected variable positions, is synthesized.

Various synthesis strategies may be employed to facilitate the identification of specific-sequence peptides having a desired activity in a screen using the library. For example, a reduced-complexity set of amino acids may be employed in the synthesis at the variable positions, to reduce the number of pools that must eventually be screened to identify an active specie.

In one synthesis strategy, two or more sets of combinatorial libraries are synthesized. In each set, one or more selected "variable" residue positions have one of substantially all possible different residues in each of the selected positions, and the remaining one or more "variable" residue positions include substantially all possible combinations of the different residues.

For purposes of illustration, one such library composition will be described with respect to a composition containing 6 variable residues in which the allowed residues include some or all of the standard 20 L-amino acids (with the exception of proline). Further, the library will be described only in reference to the variable residues, with the understanding that in the α-helical peptides suitable for use with the present invention, these variable residues are not all typically adjacent one another, but rather, may be separated from one another by invariant residues.

Figures 10A, 10B, 10C, 11A, 11B:
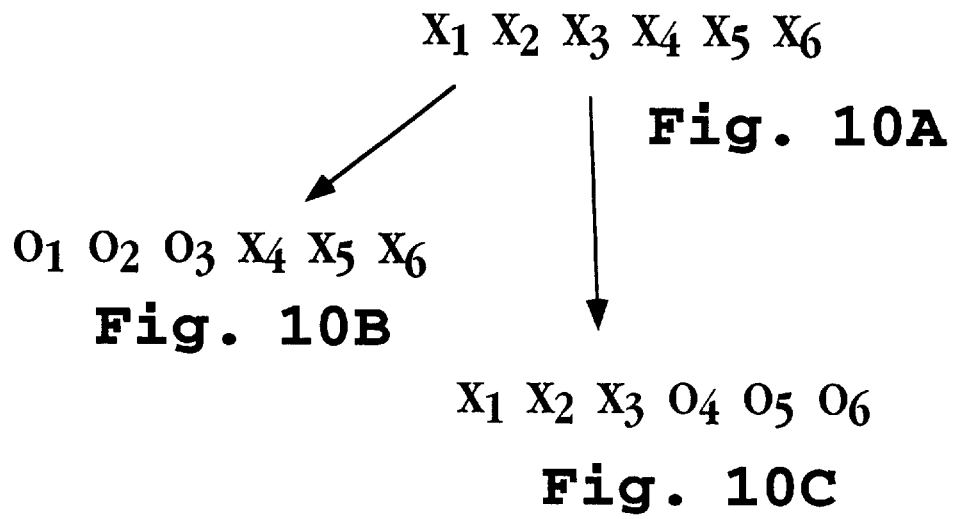
FIGS. 10A–10C are representations of combinatorial libraries of peptides with six variable positions having different residues $X_i$ at variable positions 1–6 (FIG. 10A), and two complementary sets of libraries (FIGS. 10B and 10C) showing the variable positions.
FIGS. 11A and 11B show representative peptides with variable residues corresponding to those represented in FIGS. 10B and 10C, respectively.

FIGS. 10A–10C show a general sequence of six variable residues, where the peptides containing the residues comprise two library sets. The sequence in FIG. 10A contains six residues "X" at variable positions 1–6. The first library set, illustrated in FIG. 10B, is formed by filling each of the first three variable positions, indicated by $O_1$, $O_2$, and $O_3$, with each of the 19 possible naturally-occurring amino acid residues (not counting proline). Each of the $O_1O_2O_3$ permutations will then form one library in the set, with the remaining variable positions $X_4$, $X_5$, and $X_6$ in each library preferably containing all or substantially all combinations of the different residues placed in variable positions 4–6.

Sequences of variable residues of representative members of this library set are shown in FIG. 11A, where each library contains one of the 6,859 possible three-residue permutations in its first three variable position, such as permutations AAA, AAR, ARA, and so on to VVV. The last three variable positions, i.e., variable positions 4–6 in each of these 6,859 libraries, preferably contain all or substantially all of the 6,859 combinations of the different residues. That is, each library in a set includes a known sequence of residues at variable positions 1–3, and a combinatorial library of sequences at variable positions 4–6.

The second set of libraries in the composition is shown at FIG. 10C. Each library in this set is formed by filling each of the last three variable positions, indicated by $O_4$, $O_5$, and $O_6$, with each of the possible residues, with the remaining variable positions $X_1$, $X_2$, and $X_3$ in each library preferably containing all or substantially all combinations of the different residues placed in variable positions 1–3.

Sequences of variable residues of representative members of this library set are shown in FIG. 11B, where each library contains one of the 6,859 possible three-residue permutations in its last three variable position, such as permutations AAA, AAR, ARA, and so on to VVV. The first three variable positions, i.e., variable positions 1–3 in each of these 6,859 libraries preferably contain all or substantially all of the 6,859 combinations of the different residues. That is, each library in a set includes a known sequence of residues at variable positions 4–6, and a combinatorial library of sequences at variable positions 1–3.

The two library sets are complementary in that together, they include a combinatorial library for each of a known residue permutation at variable positions 1–3 and 4–6.

The synthesis and selection procedures in the method detailed above may be simplified by employing "representative" amino acids at the variable positions. Such representative amino acids typically include between about 8–12 amino acids that are representative of most of all of the commonly classified groups of amino acids, based on the physico-chemical properties of the amino acids. These properties include the size, hydrophobicity, charge, and/or structure-forming properties that the side chains impart on the amino acid. Libraries generated using such a reduced set of representative amino acids are termed reduced combinatorial peptide libraries, or RCPLs.

One recognized grouping of amino acids by physico-chemical properties includes the groups (a) Ala, representing a small, uncharged side chain; (b) Glu and Asp, representing negatively charged amino acids; (c) Phe, Tyr, and Trp, representing side chains with aromatic groups; (d) Gly, representing a very small side chain and one which confers high flexibility of backbone conformation, (e) Ile and Val, representing β-branched, hydrophobic side chains; (f) Lys, His, and Arg, representing positively charged amino acids; (g) Leu, Met, and Cys, representing large hydrophobic and sulfur-containing side chains; (h) Pro, representing a side chain with a strong influence on secondary structure, and in particular, on turns; (i) Gln and Asn, representing amide-containing side chains; and (j) Ser and Thr, representing hydroxyl-containing side chains.

One exemplary "representative" set of amino acids suitable for use with the combinatorial libraries of the present invention includes the nine amino acids Ala (A) from group (a); Glu (E) from group (b); Phe (F) from group (c); Gly (G) from group (d); Ile (I) from group (e); Lys (K) from group (f); Leu (L) from group (g); Gln (Q) from group (i); and Ser (S) from group (j). Pro (P) from group (h) is not included because proline destabilizes α-helices by introducing kinks into the helix.

As can be appreciated, this group of amino acids reduces the number of libraries in the three-position library sets described with reference to FIGS. 10A–C and 11A–B from 6,859 to 729 (9×9×9), and similarly reduces the number of combinations in each combinatorial library from 6,859 to 729. That is, each of the 729 libraries in each set includes now only 729 different sequences in variable positions 4–6, for the first library set, and at variable position 1–3, for the second library set.

Variations on the above-described approaches may be employed. For example, in a case where the total number of variable residues is six, as above, the composition may be divided into three library sets, with pairs of residues giving rise to the permutations within a single library set. Thus, if 19 amino acids were used at each variable position, each library in the first set would contain one of the 361 possible two-residue permutations in its first two variable positions, such as permutations AA, AR, RA, and so on to VV. The last four variable positions, i.e., variable positions 3–6 in each of these 361 libraries preferably contain all or substantially all of the 130,321 combinations of the different residues at variable positions 3–6. That is, each library in a set includes a known sequence of residues at variable positions 1 and 2, and a combinatorial library of sequences at variable positions 3–6. The second and third sets are formed correspondingly. The three library sets are complementary in that together, they include a combinatorial library for each of a known residue permutation at variable positions (1,2), (3,4), and (5,6).

By way of example, to prepare a library set of 100 combinatorial peptide libraries having six variable positions (using 9 representative amino acids only), in which the first two variable positions are known, and the remaining four variable positions are combinatorial, one would distribute resin into 81 different reaction wells, and form the 81 different permutations of amino acids at the first two variable residues formed on the resin. Thereafter, at each variable residue, each reaction well would be reacted stepwise with a mixture of the 9 different residues, effectively placing each of the possible residues at the third variable position in each of the 81 libraries. This latter reaction involving a mixture of all amino acids is then repeated for the fourth, fifth, and sixth variable residue positions, to form the desired library set. The general reaction chemistry may follow standard methods (e.g., Holm and Meldal; Meldal, et al.).

A second library set having known residue positions in the third and fourth variable position is similarly formed by first carrying our the first and second coupling reactions with amino acid mixtures in a single vessel, carrying out the third and fourth coupling reactions in 100 separate wells with different known combinations of two residues in each well, and the fifth and sixth reactions with the amino acid mixtures again, but in the separate wells. The final library set with known permutations of amino acids at the fifth and sixth variable positions is similarly formed, carrying out the first four variable position additions in a single vessel with amino acid mixtures, and the final two additions in separate wells.

VIII. Method of Selecting High-Affinity Peptides

This section describes methods of generating a peptide compound capable of interacting specifically with a selected macromolecular ligand, employing a combinatorial library composition such as is described above. In the method, each library in the library set is screened for its ability to interact specifically with a selected ligand, such as a macromolecular receptor. This reaction is typically a binding reaction, as measured by the formation of a binding complex between the ligand and one or more molecules in the library being screened.

The ligand is any biological receptor of interest, that is, one for which it is desired to identify a compound that binds specifically to the receptor, to affect the functioning of the receptor in its normal physiological setting. For example, the receptor may be an enzyme, where the compound is able to bind to the active site of the enzyme or otherwise inhibit or affect the action of the enzyme on a normal substrate.

In one embodiment, the receptor may be a cell receptor protein, such as an ion channel or other transport receptor protein, or a receptor site for a hormone or other cell effector, or a receptor site for binding of pathogenic bacteria or viruses to a cell surface. The receptor protein may be associated with isolated cells with culture cells, with biological membrane particles isolated from tissues, with cells which are transformed to produce the receptor recombinantly, or with isolated cell receptors. Receptor proteins of this type, and expressed or isolated in a variety of forms, have been described in the literature.

In a related embodiment, the receptor is an antibody or antibody fragment, where it is desired to identify an "artificial" epitope that binds specifically and with high affinity to the antibody.

Figure 12A:
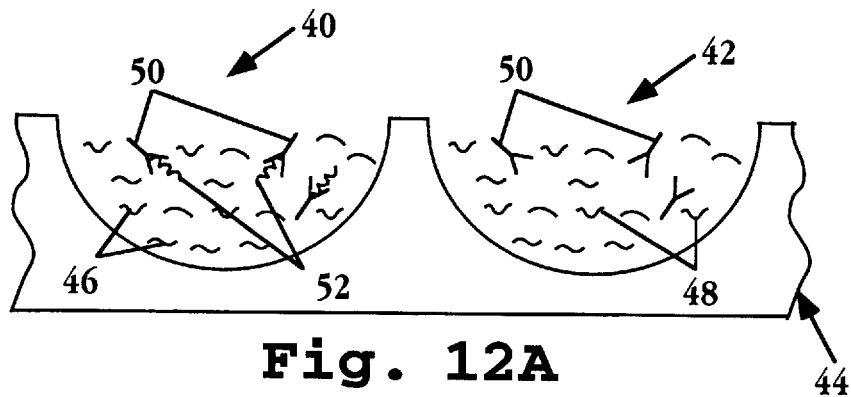
FIGS. 12A–12C illustrate steps in a method of screening libraries for the presence of peptides having specific binding affinity for an antibody receptor.
Figure 12B:
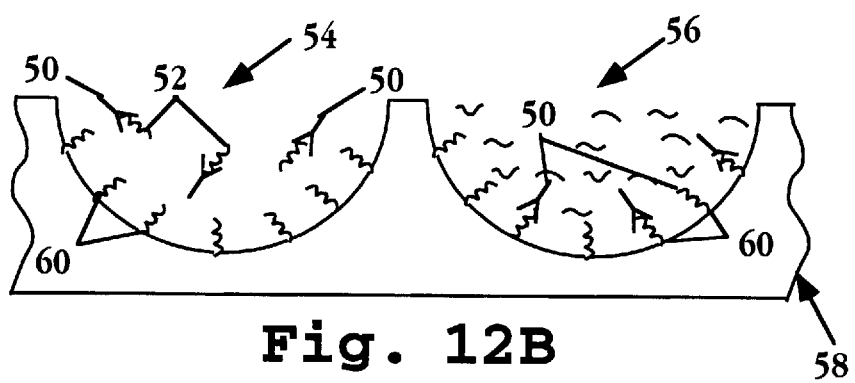
Figure 12C:
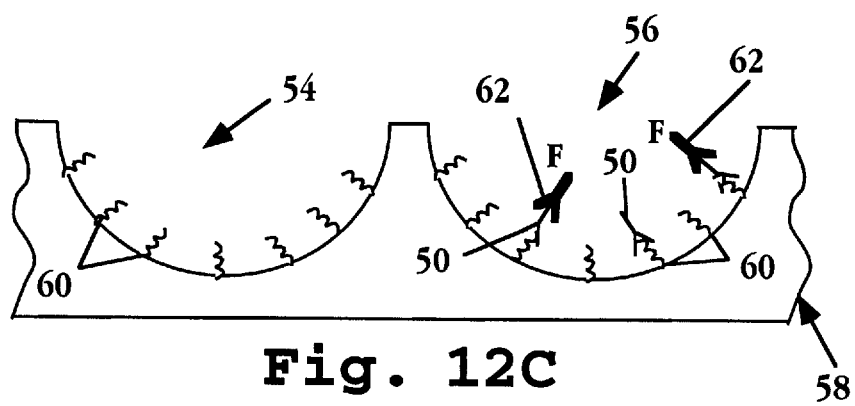

FIGS. 12A–12C illustrate one method for screening combinatorial libraries, in practicing the method of the invention. In this method, the combinatorial libraries are screened in solution phase. FIG. 12A shows two wells 40, 42 in a microtitre plate used in the testing method. Each well in the plate, such as well 40, includes one of the combinatorial libraries to be tested, where each library is made up of peptides having known residues in selected variable positions, and which are combinatorial in remaining variable positions, as described above. The library in well 40 is composed of peptides, such as peptides 46, and those in well 42, of peptides, such as peptides 48.

Each library is preincubated with a low molar concentration of a ligand, in this example, an antibody, as indicated at 50. The antibodies are immunoreactive with one or more peptide species, such as indicated at 52, in the library in well 40, but not with the library in well 42.

The reaction mixture from each library is then added to a new well on a second plate, one library per well. As seen in FIG. 12B, the second wells, such as wells 54, 56 in plate 58, are each coated with antigen molecules, such as indicated at 60. These antigens are also immunoreactive with the receptor antibody. The added libraries are now allowed to react with the surface-bound antigen under conditions allowing immune complex formation between receptor antibody molecules are surface-bound antigen. As can be appreciated from FIGS. 12B, formation of an antibody-peptide immunocomplex prevents antibody binding to the well surface (well 54). Conversely, in the absence of such complex formation, antibody becomes bound at maximum levels to the well surface (well 56).

Following this binding step, the wells are washed to remove unbound material, and reacted with reporter-labeled antibody, such as indicated at 62 in FIG. 12C. In wells containing bound receptor antibody, such as well 56 in FIG. 12C, the reporter-labeled antibody becomes bound to the well surface through the receptor antibody, as indicated. After washing the wells to remove unbound antibody, the wells are analyzed for the presence of bound reporter. The library or libraries in a set which are selected by this method are those that show low levels or the absence of bound reporter. The screening steps just described are repeated for each of the library sets. For each set, one or more libraries showing high affinity binding to the receptor are identified.

Having identified in this manner, high-affinity residues for all of the variable positions in the library peptides the next step is to construct a permutation library of peptides containing the high-affinity residues at the variable positions. Each member of the permutation library is then tested to identify the highest affinity peptides in the library. This may be done, for example, by determining the binding affinity of each library peptide for the receptor, according to standard methods.

Figure 6:
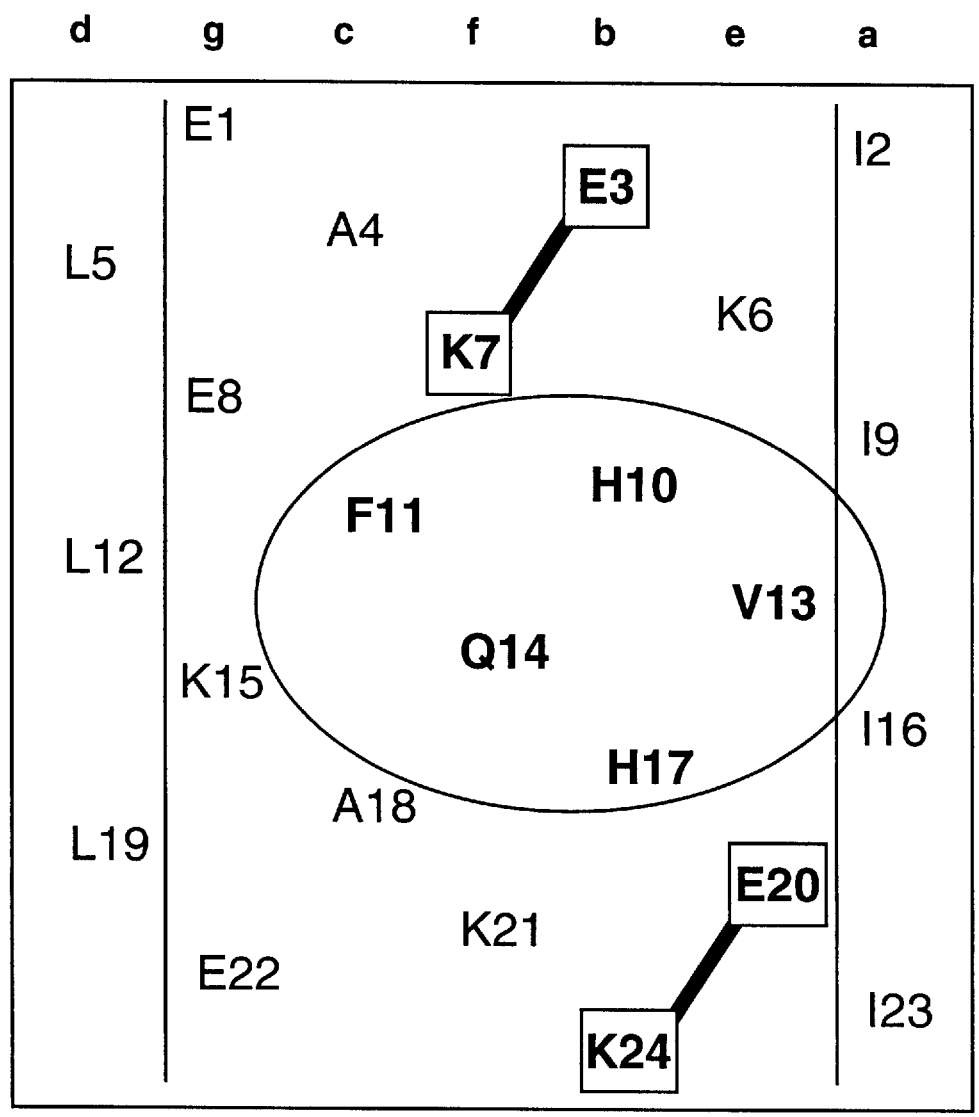
FIG. 6 shows a helical net representation of an α-helix formed of the peptide shown in FIG. 5A (SEQ ID NO:12).

Example 6, below, details a screen to measure the interaction of a polypeptide dimer composition of the present invention with an antibody directed against a monoclonal IgA directed against the lipopolysaccharide (LPS) of *Shigella flexneri*. The peptide composition is shown in FIGS. 5A, 5B and 6. FIG. 5A shows the peptide sequence (SEQ ID NO:12). The peptide is based on the "generic" peptide shown in FIG. 3A, with the variable positions $X_1$, $X_2$, $X_3$, $X_4$ and $X_5$ containing the residues H, F, V, Q, and H, respectively. FIG. 5B shows a helical wheel representation of a coiled-coil homodimer formed by association of two peptides having the sequence in FIG. 5A (SEQ ID NO:12). FIG. 6 shows a helical net representation of an α-helix predicted from the sequence shown in FIG. 5A (SEQ ID NO:12).

Figure 7:
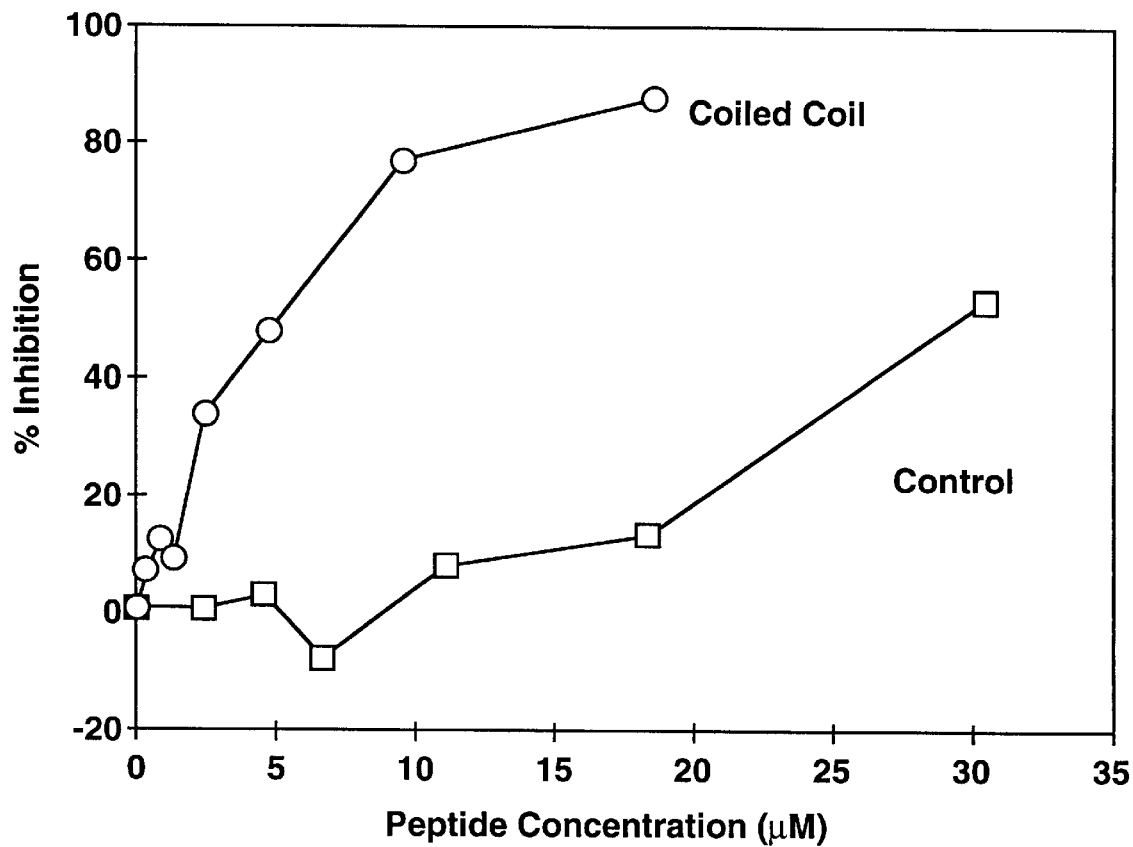
FIG. 7 shows the percent inhibition of antibody binding by coiled-coil and control peptides in a competitive ELISA assay.

The coiled-coil heterodimer made using the peptide SEQ ID NO:12 containing the lactam bridges indicated in FIGS. 5A and 5B, a composition containing the identical peptide, but without the lactam bridges, a similar control peptide (SEQ ID NO:13, FIG. 9) that did not form dimers, and a shorter linear peptide (SEQ ID NO:14, FIG. 9) having a sequence corresponding to the epitope recognized by the antibody, were tested in a competitive ELISA assay (Example 6), in a manner similar to that described in reference to FIGS. 12A–C, for affinity for the anti-LPS IgA antibody. Results of the experiments are summarized in Tables 3 and 4, below, and plotted as a function of peptide concentration in FIG. 7.

The experiments described above demonstrate that α-helices, stabilized by lactam bridges and/or coiled-coil dimer formation, constitute an effective scaffold for the presentation of a set of amino acid side chains that specifically interacts with a selected macromolecular ligand, such as a receptor or enzyme.

As described above, library compositions of the present invention may be used in a variety of different screens, including various in vitro assays and in vivo assays. Bioassays are particularly suitable for detecting binding to ligands associated with the cell membrane, such as ion channels and membrane-associated receptors. Some advantages of using methods and compositions of the present invention, as opposed to combinatorial libraries containing conformationally-unrestrained peptide oligomers, for screens involving membrane-associated receptors and ion channels, are detailed below.

IX. Applications

The various aspects and embodiments of the invention discussed above demonstrate the advantages of combining combinatorial selection methods (i.e., screens employing combinatorial libraries) with the rational design of structure-inducing templates for the selectable sequences. Combinatorial libraries of the present invention, comprised of peptides with predetermined structure, enable selection-driven peptidomimetic design, whereby a conformational model for the peptide pharmacophore is directly derived from the screening, and accordingly allow the design of a suitable non-peptidic scaffold to replace the peptide backbone.

In addition, the present invention enables the design and synthesis of a panel of libraries of assembled pharmacophores, each one characterized by a defined structure, and collectively exploring a large shape space. Each ligand selected from such libraries directly yields the information necessary to start the last step in the design of a peptide mimic. Systematic screening of the panel further enables the synthesis of secondary libraries spanning a narrower shape space.

Methods and compositions of the present invention have additional advantages in cases where the binding site of the receptor for which a high-affinity ligand is sought is composed of two or more spatially-separated domains. Such receptors are typically known to interact with polypeptides having at least 20 amino acid residues. Whereas such a binding site might not be fully bound/activated by short oligomer species such as are typically found in ordinary combinatorial libraries, the binding site may be activated by a somewhat bulkier, more rigid species such as is described herein. Examples of such binding sites include various toxin binding sites on a variety of receptors and ion channels. The toxins which form high-affinity ligands for such sites are typically larger molecules with a relatively rigid structure and two or more regions important for binding to the receptor. Many such toxins are peptide toxins that are conformationally-constrained by disulfide or other covalent cross-links. For example, the Pacific cone shells contain many ion channel-directed toxins (Olivera, et al., 1985), including ω-conotoxins, which block some calcium channels irreversibly at picomolar concentrations (McClesky, et al., 1987; Aosaki and Kasai, 1989; Plummer, et al., 1989).

The following examples illustrate but in no way are intended to limit the present invention.

MATERIALS AND METHODS

A. Abbreviations

AcCN, acetonitrile; BOP, benzotriazol-1-yl-oxy-tris-(dimethylamino)-phosphonium hexafluorophosphate; CD, circular dichroism; 2-ClZ, 2-chlorobenzyloxycarbonyl; Fmoc, 9-fluorenylmethyloxycarbonyl; GRH, growth hormone releasing factor; HFIP, 1,1,1,3,3,3-hexafluoroisopropanol; HF, hydrofluoric acid; HBTU, 2-(1H-benzotriazolyl)-1,1,3,3-tetramethyluronium hexafluorophosphate; HOBt, 1-hydroxybenzotriazole; NMM, N-methylmorpholine; NMP, N-methylpyrrolidinone; OBzl, benzyl; OFm, 9-fluorenylmethyl; RPC, reversed-phase chromatography; TFA, trifluoroacetic acid; TFE, 2,2,2-trifluoroethanol.

EXAMPLE 1

Peptide Synthesis, Purification and Analysis

Peptides were synthesized by solid-phase peptide synthesis using a benzhydryl amine-hydrochloride resin on a Labortec SP 640 peptide synthesizer (Bubendorf, Switzerland). All amino acids were N-α-t-butyloxycarbonyl protected with lysine and glutamic acid side-chains functionalities protected as 2-ClZ and OBzl derivatives, respectively. The side-chains of glutamic acid and lysine residues involved in lactam formation were protected as OFm and Fmoc derivatives, respectively. A coupling protocol using a five-fold excess of HBTU/HOBt/amino acid/NMM (1:1:1:1.5) in NMP with a 5 minute activation time was employed. In some peptides, lactam bridges were incorporated as described in Example 4.

The peptides were cleaved from the resin by reaction with hydrofluoric acid (HF; 10 ml/g resin) containing 10% anisole and 2% 1,2-ethanedithiol for 1 hour at −5° C. to 0° C. The crude reduced peptides were purified by reversed-phase high performance liquid chromatography (RPC) on a "SYN-CHROPAK" RP-4 preparative $C_4$ column (250×21.2 mm inner diameter, 6.5 μm particle size, 300 Å pore size; SynChrom, Lafayette, Ind.) with a linear AB gradient of 0.1% B/min and 5 ml/min, where solvent A was 0.05% trifluoroacetic acid (TFA) in water and solvent B was 0.05% TFA in acetonitrile.

For amino acid analyses, purified peptides were hydrolyzed in 6N HCl containing 0.1% phenol for 1 hour at 160° C. in evacuated sealed tubes. Amino acid analysis was performed on a Beckman model 6300 amino acid analyzer (Beckman, San Ramon, Calif.). The correct primary ion molecular weights of the reduced peptides were confirmed by plasma desorption time of flight mass spectroscopy on a "BIOION-20" Nordic mass spectrometer (Uppsala, Sweden).

EXAMPLE 2

Circular Dichroism Measurements

Circular dichroism (CD) spectra were recorded at 20° C. on a Jasco J-500C spectropolarimeter (Jasco, Easton, Md.) equipped with a Jasco DP-500N data processor and a Lauda (model RMS) water bath (Brinkmann Instruments, Rexdale, Ontario, Canada) for control of the temperature of the cuvette. Constant $N_2$ flushing was employed. The instrument was routinely calibrated with an aqueous solution of recrystallized d-10-(+)-camphorsulfonic acid at 290 nm.

Molar ellipticity is reported as mean residue molar ellipticity ([θ], deg•cm²•dmol¹) and calculated from the equation:

$$[\theta] = \theta_{obs} \times mrw/10 \times 1 \times c$$

where $\theta_{obs}$ is the ellipticity measured in degrees, mrw is the mean residue molecular weight (molecular weight of the peptide divided by the number of amino acid residues), c is the peptide concentration in grams per milliliter, and 1 is the optical path length of the cell in centimeters.

CD spectra were the average of four scans obtained by collecting data at 0.1 nm intervals from 250 to 190 nm. Peptide concentrations were determined by amino acid analysis. The pH was measured at room temperature.

EXAMPLE 3

Heterodimer vs. Homodimer Formation

Two peptides, EE (SEQ ID NO:1) and KK (SEQ ID NO:2), were synthesized as described in Examples 1 and 4. CD spectra of peptide mixtures of different ratios of the first subunit peptide (EE; SEQ ID NO:1) and the second subunit peptide (KK; SEQ ID NO:2) were measured as described in Example 2, to determine the degree of heterodimer vs. homodimer formation.

The peptides were suspended in a solution containing 0.1 M KCl and 50 mM potassium phosphate buffer, pH 7 at 20° C. (reaction buffer). The total peptide concentration (sum of EE and KK concentrations) was 196 μM for all measurements.

The data show that as the ratio of the peptides is changed from 0:100 to 50:50, the conformation of the peptide mixture is changed from a random coil structure to an α-helical structure. An equimolar mixture of the EE and KK peptides displays the double minima at 220 and 208 nm with −31,000 deg•cm²•dmol⁻¹ of mean residue ellipticity at 220 nm, which corresponds to ~100% α-helical structure (Hodges, et al., 1990), suggesting that the interhelical ionic repulsions which destabilize the homo-stranded coiled-coil provide a driving force for the formation of the hetero-stranded coiled-coil.

These results indicate that the mixture of peptides EE and KK forms a hetero-stranded coiled-coil.

EXAMPLE 4

Creation of Lactam Bridges

Peptides containing lactam bridges were synthesized as described in Example 1. Double couplings with 5 equivalents of 2-(1H-benzotriazol-yl)-1,1,3,3-tetramethyluronium hexfluorophosphate (HBTU), 1-hydroxybenzotriazole (HOBt) and Boc amino acids and 7.5 equivalents of N-methylmorpholine (NMM) in N-methylpyrrolidone (NMP) were utilized for each cycle. During each cycle, the Boc group was removed with 50% trifluoroacetic acid (TFA) in methylene chloride (DCM).

Cyclizations involving the side chains of lysine and glutamic acid residues (lactam bridges) were formed on the resin by deprotection of the desired side-chains with 20% piperidine in NMP followed by cyclization with five-fold excess of HBTU/HOBt/NMM in NMP with 5% HFIP (Felix, et al., 1988). To facilitate the intrachain reaction, substitution levels were maintained at or below 0.15 mmol of amino groups per gram of resin. Substitution levels were determined spectrophotometrically according to the method of Meienhofer, et al., (1979).

The ε-amino group of lysines 35 and 7 and the γ-carboxyl group of glutamic acids 31 and 3 for both peptides EE (SEQ ID NO:1) and KK (SEQ ID NO:2) were protected with Fmoc and OFm groups, respectively. This allowed for the selective deprotection of these residues with 20% piperidine prior to the solid phase cyclization with 3 equivalents of HBTU, HOBt and 4.5 equivalents of NMM in NMP. The synthesis of the C-terminal heptad of peptide EE, shown in FIG. 2, serves to outline the cyclization procedure. Other lactam bridges were prepared similarly.

A. Preparation of BocLys(Fmoc)-Benzhydrylamine Resin (Labortec SP 640 Peptide Synthesizer)

Benzhydrylamine resin (3.0 g, 0.74 meq/g resin, 2.2 meq) was washed with 30 mL each of DCM, methanol (MeOH), DCM, 5% diisopropylethylamine (DIEA) in DCM (×2) DCM, and NMP (×2). BocLys(Fmoc) (1.14 g, 2.4 mmol), HBTU (0.91 g, 2.4 mmol), HOBt (0.37 g, 2.4 mmol) were dissolved in NMP (15 mL) to which was added NMM (0.51 mL, 3.63 mmol) and solution was preactivated for 5 minutes. This solution was added to the swelled resin and allowed to stir for 5 minutes. The resultant BocLys(Fmoc)-resin was washed with NMP (2×1 min) and DCM (3×1 min).

B. Preparation of the C- and N-Terminal Heptads

After deprotection (50% TFA in DCM, 1×20 min) and neutralization (5% DIEA in DCM, 2×2 min) the resin was washed with DCM (2×1 min) and NMP (3×1 min). The next amino acid and all following amino acids for the C-terminal heptad and subsequent amino acids of the N-terminal heptad were double coupled according to the following protocol.

Boc amino acid (5 eq.), HBTU (5 eq.), HOBt (5 eq.) were dissolved in NMP (15 mL) to which was added NMM (7.5 eq.) and the solution was allowed to preactivate for 5 minutes. This solution was added to the reaction vessel and allowed to gently agitate for 30 minutes. One cycle of the synthesis consisted of the following operations (10 mL of solvent per gram of resin): 1) 50% TFA in DCM (1×1 min); 2) 50% TFA in DCM (1×20 min); 3) DCM (3×1 min); 4) 5% DIEA in DCM (2×2 min); 5) DCM (1×1 min); 6) NMP (3×1 min); 7) couple (30 min); 8) NMP (3×1 min); 9) couple (30 min); 10) NMP (2×1 min); 11) DCM (3×1 min).

C. Lysine-Glutamic Acid Side Chain Cyclizations

After addition of Boc-Ile, selective deprotection of the Fmoc group of lysine and OFm group of glutamic acid was performed with 20% piperidine in DCM (1×20 min) and the resin was subsequently washed with DCM (2 ×1 min) and NMP (3×1 min). Cyclizations were performed using the following protocol.

HBTU (3 eq.) HOBT (3 eq.) and NMM (4.5 eq.) were dissolved in NMP to which was added 0.5 mL of hexafluoroisopropanol. The solution was added to the reaction vessel and allowed to gently agitate for 8 hours. The progress of the reaction was monitored by quantitative ninhydrin test (Sarin, et al., 1981). Typically, three coupling were required to achieve coupling efficiency of greater than 97%. The resin was acetylated for 1 hour with 10 equivalents of acetic anhydride in 25 mL of 5% DIEA in DCM and washed with DCM, MeOH, DCM and NMP (×2). The following steps were employed for each cyclization: 1) 20% piperidine in DCM (1×1 min); 2) 20% piperidine in DCM (1×20 min); 3) DCM (2×1 min); 4) NMP (3×1 min); 5) couple (8 h); 6) NMP (2×1 min); 7) DCM (1×1 min); 8) 5% DIEA in DCM (1×1 min); 9) DCM (1×1 min); NMP (2×1 min) 11) couple (3 h); 12) repeat steps 6–10; 13) couple (1 h).

EXAMPLE 5

Effects of Lactam Bridges on Helical Content of Peptides in Solution

A series of peptides containing lactam bridges at various positions were designed and synthesized as detailed in Example 1. The sequences of the peptides are provided in Table 1, below, and in the Sequence Listing. Table 1 also shows the locations of the lactam bridges and the peptide names.

TABLE 1

AMINO ACID SEQUENCES OF LACTAM BRIDGED AND LINEAR PEPTIDES

| Peptide No. | SEQ ID NO: | Sequence | Lactam Position | No. of Lactam Bridges | Peptide Name |
|---|---|---|---|---|---|
| 1 | 7 | Ac-EIEALKKEIEALKK-amide | $Lys_7$—$Glu_{10}$ | 1 | KE (i, i + 3) |
| 2 | 7 | Ac-EIEALKKEIEALKK-amide | $Lys_6$—$Glu_{10}$ | 1 | KE (i, i + 4) |
| 3 | 7 | Ac-EIEALKKEIEALKK-amide | $Glu_3$—$Lys_6$, $Glu_{10}$—$Lys_{13}$ | 2 | 2EK (i, i + 3) |
| 4 | 7 | Ac-EIEALKKEIEALKK-amide | $Glu_3$—$Lys_7$, $Glu_{10}$—$Lys_{14}$ | 2 | 2EK (i, i + 4) |
| 5 | 7 | Ac-EIEALKKEIEALKK-amide | — | 0 | Linear 5 |

TABLE 1-continued

AMINO ACID SEQUENCES OF LACTAM
BRIDGED AND LINEAR PEPTIDES

| Peptide No. | SEQ ID NO: | Sequence | Lactam Position | No. of Lactam Bridges | Peptide Name |
|---|---|---|---|---|---|
| 6 | 8 | Ac-EIEALEKEIKALKK-amide | Glu$_6$—Lys$_{10}$ | 1 | EK (i, i + 4) |
| 7 | 8 | Ac-EIEALEKEIKALKK-amide | — | 0 | Linear 7 |
| 8 | 9 | Ac-EIKALKEEIKALKE-amide | Lys$_3$—Glu$_7$, Lys$_{10}$—Glu$_{14}$ | 2 | 2KE (i, i + 4) |
| 9 | 9 | Ac-EIKALKEEIKALKE-amide | — | 0 | Linear 9 |
| 10 | 10 | Ac-EIQALKK(Ac)EIQALKK(Ac)-amide | — | 0 | Linear 10 |

The lactam bridge designation contains the sequence of the two residues involved from the N-terminal of the peptide in one letter code which gives the orientation of bridge and the bridge type as either i to i+3 or i to i+4. Peptides with two lactam bridges are designated by the number 2 preceding the sequence. Peptides with no lactam bridges are denoted as linear followed by the peptide number. The lactam bridge designation contains the sequence of the two residues involved from the N-terminal of the peptide in one letter code which gives the orientation of bridge and the bridge type as either i to i+3 or i to i+4. Peptides with two lactam bridges are designated by the number 2 preceding the sequence. Peptides with no lactam bridges are denoted as linear followed by the peptide number.

The lactam bridges were incorporated between the sidechains of glutamic acid and lysine residues at the N- or C-termini or in the middle of the peptide at (i, i+3) or (i, i+4) spacings. The (i, i+n) nomenclature refers to the relative positions of the residues between which the bridge is formed in the peptide sequence. For example, a lactam bridge formed between a Lys at position 7 and a Glu at position 10 is an (i, i+3) bridge, while a bridge formed between a Lys at position 6 and a Glu at position 10 is an (i, i+4) bridge. The repetitive nature of an α-helix (3.6 residues per turn) dictates that lactam bridges formed between residues spaced (i, i+3) or (i, i+4) will fall on the same face of the helix. Where sequence changes were made to study different orientations of the lactam bridge (Glu-Lys vs. Lys-Glu) the linear homolog was synthesized as a control.

All peptides were 14 residues in length and contained an equal number of acidic and basic amino acids. Glutamic acid residues were located near the N-terminus and lysine residues near the C-terminus such that the interaction of these charged side-chains with the helix dipole would be attractive in nature and enhance helicity (Shoemaker, et al., 1985, 1987). In addition, the Ile and Leu residues were arranged in a 3,4 hydrophobic repeat in which they occupied positions a and d of the repeating heptad denoted abcdefg, characteristic of a two stranded α-helical coiled-coil, in order to facilitate peptide dimerization through this hydrophobic face and increase helical content. Ile was selected for the position a and Leu for position d to provide maximal stability of the peptide dimer. The N- and C-termini were capped with an acetyl and carboxamide functionalities, respectively in order to avoid unfavorable helix-dipole interactions (Shoemaker, et al., 1985, 1987).

Helical content of the peptides was measured using far-ultraviolet CD spectra, as detailed in Example 2. Spectra were measured at a peptide concentration of 750 μM±30 μM to avoid any concentration dependency effects. Results of the experiments are summarized in Table 2, below.

TABLE 2

CIRCULAR DICHROISM RESULTS OF LACTAM BRIDGES
AND LINEAR PEPTIDES

| | [Θ]$_{222}$ (deg · cm$^2$/dmol$^{-1}$)[a] | | Δ[Θ]$_{222}$[b] (Benign- 50% TFE) | Δ[Θ]$_{222}$[c] (Linear- Lactam Benign) | Helix Content (%)[d] | |
|---|---|---|---|---|---|---|
| Peptide | Benign | TFE | | | Benign | 50% TFE |
| KE i (i + 3) | −3600 | −19850 | 16250 | −15000 | 12 | 64 |
| KE i (i + 4) | −9000 | −28400 | 19400 | −9600 | 29 | 92 |
| 2EK i (i + 3) | −3800 | −9900 | 6100 | −14800 | 12 | 32 |
| 2EK i (i + 4) | −30350 | −32150 | 1800 | 11750 | 99* | 105 |
| Linear 5 | −18600 | −30000 | 11400 | — | 61 | 98 |
| 2KE i (i + 4) | −8300 | −29100 | 20800 | 4650 | 27 | 95 |
| Linear 7 | −3650 | −23500 | 19850 | — | 12 | 77 |
| EK i (i + 4) | −21800 | 29200 | 7400 | 10100 | 71* | 95 |
| Linear 9 | −11700 | −28900 | 17200 | — | 38 | 94 |
| Linear 10 | −2900 | −14000 | 11100 | — | 10 | 45 |

[a]calculated molar ellipticity of the peptide at 222 nm.
[b]Δ[Θ]$_{222}$ is the difference between the ellipticity at 222 nm in benign buffer and in 50% TFE.
[c]Δ[Θ]$_{222}$ is the difference between the ellipticity at 222 nm of the linear peptide and lactam peptide of the same sequence.
[d]The % helical content was calculated from the ratio of the observed [Θ]$_{222}$ value divided by the predicted molar ellipticity. The predicted molar ellipticity (X$^n$H) was calculated from the equation X$^n$H = X∞H(1-k/n), using a [Θ]$_{222}$ value of −37400 for a helix of infinite length (X∞H), n equal to 14 and k the wavelength dependent constant equal to 2.50 (Chen, et al., 1974).
*Denotes the most favorable lactam bridge locations to induce helical structure in benign medium.

Under benign conditions (50 mM KH$_2$PO$_4$, 100 mM KCl, pH 7), peptides KE (i, i+3) and KE (i, i+4) showed a significant drop in helical content when compared to their linear 5 homolog. The linear peptide was approximately 61% helical whereas KE (i, i+3) and K-E (i, i+4) contained 12 and 29% helical content as calculated by the method of Chen, et al., (1974). Peptide KE (i, i+3) contained significant random structure as characterized by the minima in the CD measurement at 198 nm (Chen, et al., 1972). In 50% trifluoroethanol (TFE), a solvent which is known to promote helix formation in peptides with helical propensity (Goodman and Listowsky, 1962; Goodman, et al., 1971; Lehrman, et al., 1990; Sonnichsen, et al., 1992), peptide KE (i, i+3) was 64% helical. However, under identical conditions, linear 5 and KE (i, i+4) were 98% and 92% helical, respectively, and were characterized by a maximum at 192 nm (>60000) and minima at 208 and 220 nm.

Peptide EK (i, i+4) was considerably more helical in benign conditions than peptide KE (i, i+4) (71% vs. 29%). This increase in helicity was not attributable to sequence effects alone. Since both peptides had similar helical content in 50% TFE (>90% helicity), it is likely that the orientation of the lactam bridge in peptide KE (i, i+4) (Lys to Glu) has a destabilizing interaction between the lactam carbonyl and main chain atoms of the helix. The amount of helix stabilization imparted by the EK (i, i+4) lactam (−10100) ($\Delta[\theta]_{222}$ (linear-lactam), Table 2) is comparable in magnitude to the amount of helix destabilization that results from a KE (i, i+4) lactam (−9600).

CD spectra of peptides with lactams located at the N- and C-termini indicated that peptide 2EK (i, i+3) had a similar CD profile as peptide KE (i, i+3) and the same amount of helical content (12%, Table 2). However, the amount of helical structure induced by 50% TFE was significantly less for peptide 2EK (i, i+3) compared to KE (i, i+3) ($\Delta[\theta]_{222}$ of 6100 vs. 16250). These results suggest that the ability of (i, i+3) lactams to induce helical structure in benign medium is limited.

Similarly, peptide 2KE (i, i+4) and peptide KE (i, i+4) have nearly identical CD spectra and helical content under benign conditions (27% and 29% respectively) and in the presence in 50% TFE the helical content rises to greater than 90% (Table 2). In benign conditions, the minimum for 2KE (i, i+4) was shifted slightly from 202 to 201 nm, suggesting that the slight drop in $[\theta]_{222}$ value is a result of an increase in random structure. However, two Glu-Lys (i, i+4) lactams at the ends of the peptide resulted in a peptide, 2EK (i, i+4), that was 99% helical under benign conditions. This peptide was characterized by a maximum at 192 nm (82000) and minima at 209 nm (−27700) and 221 (−30350). There was a slight increase in $[\theta]_{222}$ value from −30350 to −32150 on the addition of TFE. Since the peptide was essentially completely helical in benign medium, the observed increase in TFE may have to do with the absorbance properties of the lactam bridged peptide in TFE rather than with helical structure.

CD spectra of 2EK (i, i+4) and its linear counterpart under benign conditions and in the presence of 50% TFE demonstrate a significant increase in helical content caused by properly located and oriented lactam bridges. The increase in helical content induced by two (i, i+4) lactams (11750) is almost identical to the helicity induced by 50% TFE for the linear peptide (11400), indicating the efficacy of lactam bridges in imparting helical structure. Another feature of the 2EK (i, i+4) spectrum was the change of the $[\theta]_{222}/[\theta]_{208}$ ratio in going from benign conditions (1.10) to 50% TFE (0.97). Further, the mean residue molar ellipticity at 222 nm showed a concentration dependency indicative of dimerization. The peptide remained greater than 95% helical over a concentration range of 6000 $\mu$M to 250 $\mu$M. The linear peptide 5 showed a concentration dependence over the entire range (6000 $\mu$M to 25 $\mu$M).

Peptide linear 10 was synthesized to determine whether the increased hydrophobicity associated with lactam formation played a role in enhancing helical content. Glutamic acid was substituted by glutamine and the ε-amino group of lysine was acetylated to impart a hydrophobicity typically associated with lactam bridges, without the constraints of cyclization. Under benign conditions, this peptide had a substantial amount of random structure with approximately 10% helical content (Table 2). In 50% TFE the helical content rose to 46% suggesting that the hydrophobicity change upon formation of lactam bridges had little or no effect on stabilizing the helical content of peptide 2EK (i, i+4). The linear 5 peptide with 2EK salt bridges had 61% helical content in benign conditions and 98% α-helix in 50% TFE (Table 2). These results suggest that the two salt bridges which are present in linear 5 and absent in linear 10 offer considerable stability to the helix.

Thermal denaturations in the presence of 25% TFE were carried out to determine the stabilizing effect of the various (i, i+4) lactams. In addition to promoting α-helix formation in peptides with helical propensity, TFE has been shown to disrupt tertiary and quaternary interactions in peptides and proteins (Sonnichsen, et al., 1992, Lau, et al., 1984). Accordingly, thermal denaturations in the presence of TFE should be a measure of the stability of single stranded α-helices.

The CD spectra of all five peptides showed an isodichroic point at 202 nm, consistent with the presence of just two conformations (Padmanabhan, et al., 1990; Engel, et al., 1991). Though all peptides had essentially the same helical content in the presence of TFE at 5° C., differences in helical content are observed as the temperature was increased. The stability of the peptides generally followed their helical content under benign conditions. The least stable peptides were the KE peptides, with 2KE (i, i+4) being substantially less stable than K-E (i, i+4), and both being less stable than the linear non-cyclized peptide, indicating that an additive destabilizing interaction was involved in the KE lactam peptides.

On the other hand, the EK lactam peptides were substantially more stable than the linear peptide. Peptide EK (i, i+4) was more stable than 2EK (i, i+4) even though under benign conditions two lactams were more effective than one lactam in promoting α-helical content. At 80° C., both peptides retained greater than 70% of their original α-helical content. The increase in α-helical content in peptide 2EK (i, i+4) probably arose from the terminal lactam bridges locking the peptide into the desired conformation and negating end effects. In the crystal structure of peptides of the coiled-coil region of GCN4, the N- and C-termini deviated from an α-helical conformation and were frayed (O'Shea, et al., 1991). Similar results were obtained from molecular dynamics simulation of model coiled-coils by Zhou, et al., (1992). For a peptide of only 14 residues, such fraying is contemplated to play a significant role in decreasing the α-helical content of the peptide. Peptide EK (i, i+4) would be expected to have frayed ends and this may account for the lesser amount of α-helical content in benign conditions.

Figure 8:
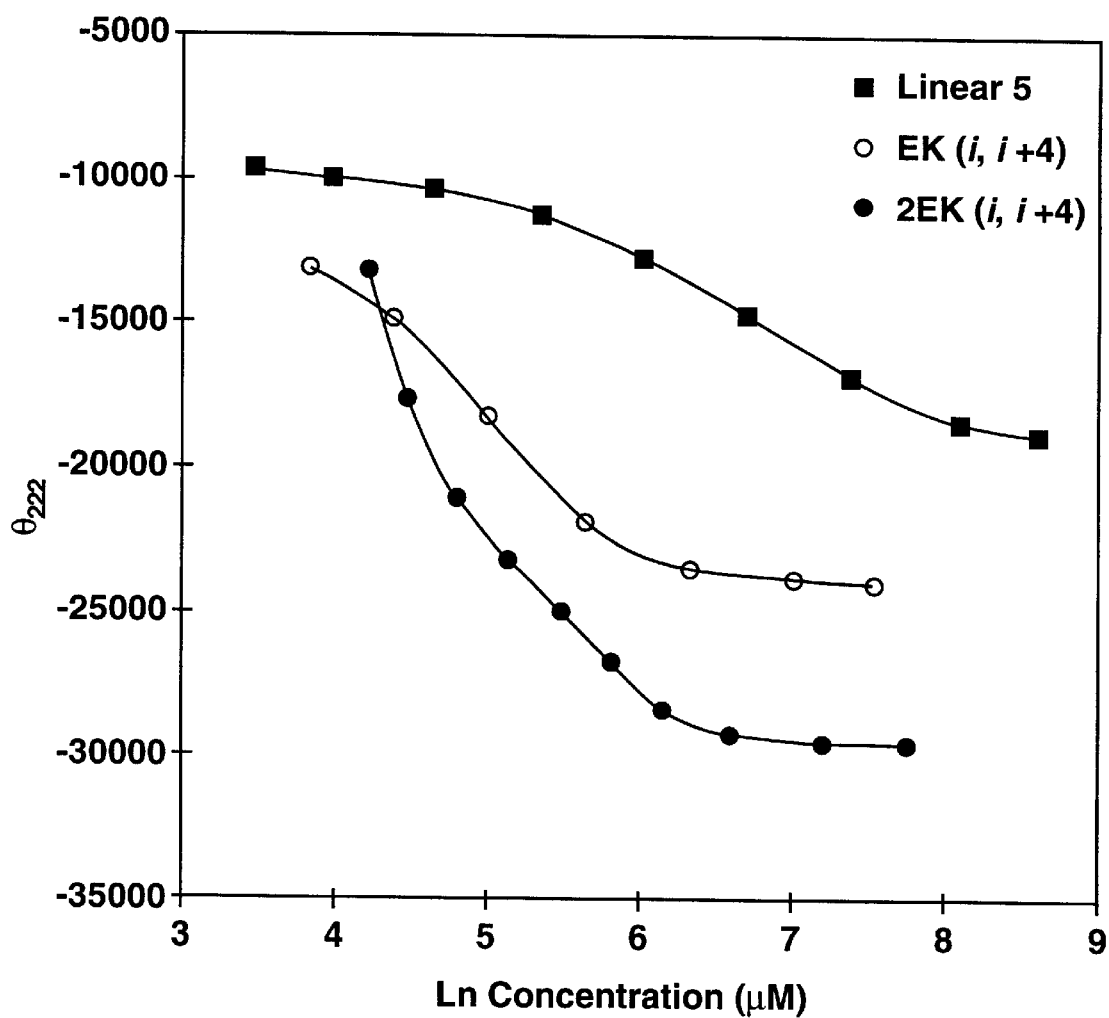
FIG. 8 shows the effect of peptide concentration on the ellipticity at 222 nm at 20° C. for peptides 2EK (i, i+4), Linear 5 and EK (i, i+4).

Data in FIG. 8 show that peptides 2EK (i, i+4) EK (i, i+4) and Linear 5 all showed a dependence of helical content on peptide concentration, suggesting that dimerization plays a significant role in stabilizing helical content, in addition to lactam bridges and salt bridges. The magnitude of the stability imparted by lactam bridges can be gleamed from these concentration dependency curves (FIG. 8). Since Linear 5 and 2 EK (i, i+4) have identical sequences and identical residues at the hydrophobic interface, the difference in helical content at any concentration is due to lactam bridges enhancing helical structure to a greater extent than Glu-Lys salt bridges.

EXAMPLE 6

Competitive ELISA Assay

Binding of the peptides represented as SEQ ID NO:12, SEQ ID NO:13 and SEQ ID NO:14 to IgAC5, a monoclonal IgA antibody reactive with the lipopolysaccharide (LPS) of *Shigella flexneri,* was measured by enzyme-linked immunosorbent assay (ELISA) using standard methods as follows. The peptides (either SEQ ID NO:12 (with or without lactam bridges), SEQ ID NO:13 or SEQ ID NO:14) (80 μl) and IgAC5 (~0.5 μg/ml) were incubated in Tris-buffered saline (TBS) for 1 hour at room temperature. The resulting peptide-antibody complexes were detected by adding 100 μl of the above solution to polystyrene 96-well microplates (Nunc-Immunoplate "MAXISORP", Fisher Scientific, Pittsburgh, Pa.), which had been coated overnight with 100 μl of a 1:20000 dilution of rabbit anti-CP1 antiserum in TBS and blocked with 0.8% bovine serum albumin (BSA) in TBS, then incubating for 1 hour at RT. The anti-CP1 antiserum was produced by immunization with the CP1 synthetic peptide, which has the sequence given as SEQ ID NO:15 (Kim and Berg, 1993; Krizek, et al., 1991).

After washing, bound peptide-antibody complexes were detected by sequential incubation with alkaline phosphate-conjugated goat anti-mouse IgA α-chain (Sigma Chemical Co., St. Louis, Mo.; 1:5000 dilution in TBS+0.8% BSA, 100 μl/well) and p-nitrophenyl phosphate (Sigma 104 tablets; 1 mg/ml in 10% diethanolamine containing 0.5 mM MgCl2, pH 9.8, 100 μl/well) at 20° C. Color development was quantified by measuring the absorbance at 405 nm on a Titertek "MULTISKAN PLUS" MK-II microplate reader (Flow Lab, Inc., McLean, Va.).

Data in table 3, below, show the % inhibition of antibody binding as a function of peptide concentration for peptides Coiled-Coil (CC; SEQ ID NO:12) with and without lactam bridges, as well as % inhibition by the linear ZnF peptide (SEQ ID NO:14). The data demonstrate that the conformationally-constrained coiled-coil peptide stabilized by lactam bridges is more effective at binding to the anti-LPS antibody than the same peptide not stabilized by lactam bridges, indicating that at least for this particular interaction, conformationally-constraining the peptide improves the coiled-coil heterodimer's ability to bind to a selected receptor. The data further demonstrate that a shorter, unconstrained peptide containing the consensus antibody binding residues (FIG. 9) is less effective at binding the antibody than either the bridged or unbridged Coiled-Coil (SEQ ID NO:12) peptide.

TABLE 3

INHIBITION OF IGAC5-ZNF BINDING BY PEPTIDES
% Inhibition

| Peptide Concentration (μM) | Coiled-Coil | CC w/o Lactams | Linear ZnF |
|---|---|---|---|
| 0.3 | 7.2 | 0.0 | 0.0 |
| 1.2 | 9.2 | 2.5 | 1.3 |

TABLE 3-continued

INHIBITION OF IGAC5-ZNF BINDING BY PEPTIDES
% Inhibition

| Peptide Concentration (μM) | Coiled-Coil | CC w/o Lactams | Linear ZnF |
|---|---|---|---|
| 2.3 | 34.4 | 6.9 | 1.7 |
| 4.6 | 48.5 | 8.6 | 8.3 |
| 9.2 | 76.5 | 14.3 | 20.8 |

Data shown in Table 4, below demonstrate that a lactam-bridged peptide, containing the consensus antibody binding residues, designed to form a non-dimerizing α-helix (Single Helix; Single-Stranded; SEQ ID NO:13) is also effective as a scaffold for the presentation of a selected set of antibody-binding residues, and that this conformationally-restricted peptide is more effective at binding the antibody than the shorter, linear antibody-binding consensus sequence peptide (Linear ZnF; SEQ ID NO:14). The peptide concentration values presented in Table 4 assume that (unbridged) Coiled-Coil peptide remains as a monomer.

TABLE 4

INHIBITION DATA ASSUMING FUNCTIONAL
CONCENTRATION OF CC IS A MONOMER
% Inhibition

| Peptide Concentration (μM) | Single Helix | Linear ZnF | Coiled-coil (Monomer) |
|---|---|---|---|
| 0.29 | | | 7.18 |
| 1.16 | | | 9.15 |
| 2.13 | | 0.0 | |
| 2.31 | | | 34.44 |
| 2.50 | 0.04 | | |
| 3.55 | | 1.3 | |
| 4.62 | | | 48.48 |
| 5.00 | 19.81 | | |
| 5.92 | | 8.7 | |
| 9.23 | | | 76.47 |
| 9.86 | | 18.3 | |
| 10.00 | 30.41 | | |
| 16.44 | | 20.8 | |
| 18.46 | | | 88.10 |
| 20.00 | 60.43 | | |
| 27.40 | | 19.6 | |
| 40.00 | 82.67 | | |
| 80.00 | 106.17 | | |

While the invention has been described with reference to specific methods and embodiments, it is appreciated that various modifications and changes may be made without departing from the invention.

It is claimed:

1. A combinatorial library of different-sequence polypeptide members, where each member of the library comprises (a) first and second polypeptides bound to one another to form an alpha-helical coiled-coil dimer scaffold characterized by (i) an internal region formed by regularly repeating, invariant, hydrophobic amino acid residues in both polypeptides, (ii) first and second exposed regions formed by regularly repeating amino acid residues in the individual first and second polypeptides, respectively, (iii) a polypeptide length of at least seven residues for each polypeptide, and (iv) a covalent intrachain bond between invariant residues in at least one of the polypeptides, effective to stabilize that polypeptide in its α-helical conformation, where the scaffold is stabilized by hydrophobic interactions among the subunits in the internal region of the scaffold and the intrachain bond, and (b) a unique variation of amino acid residues in the exposed region of at least one of the polypeptides.

2. The library of claim 1, which contains at least $10^3$ members, and amino acid variations occur in at least three different residue positions in the exposed region of the at least one polypeptide.

3. The library of claim 1, wherein amino acid variations occur at contiguous residue positions in the exposed region of the at least one polypeptide.

4. The library of claim 1, wherein amino acid variations occur at residue positions in the exposed regions of two adjacent α-helical turns in the at least one polypeptide.

5. The library of claim 1, wherein amino acid variations occur in a total of at least two different residue positions in the exposed regions of each polypeptide.

6. The library of claim 1, wherein the first polypeptide contains a terminal bridge segment linking an end of the first polypeptide to an adjacent end of the second polypeptide, the first exposed region further includes this bridge segment and amino acid variations occur in this bridge segment.

7. The library of claim 1, wherein each polypeptide contains at least four helical turns.

8. The library of claim 1, wherein said intrachain bond is a lactam bridge formed between invariant positions.

9. The library of claim 1, wherein the unique variation of amino acid residues in the exposed region is accomplished using representative amino acids that display the basic physico-chemical properties associated with naturally occurring amino acids, but exclude many of these naturally occurring amino acids.

10. The library of claim 9, wherein the representative amino acids include at least one from each of the groups consisting of (a) Ala, (b) Glu and Asp, (c) Phe, Tyr, and Trp, (d) Gly, (e) Ile and Val, (f) Lys, His, and Arg, (g) Leu, Met, and Cys, (h) Gln and Asn, and (i) Ser and Thr.

11. The library of claim 1, wherein each polypeptide contains a heptad of amino acid residues with positions denoted abcdefg, where a and d are said hydrophobic residues.

12. The library of claim 11, wherein residues a and d are each selected from the group consisting of Ile, Leu, and Val.

13. The library of claim 12, wherein residue a is Ile, and residue d is Leu.

* * * * *

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 35 amino acids
        ( B ) TYPE: amino acid
        ( C ) STRANDEDNESS: single (D) TOPOLOGY: unknown (ii) MOLECULE TYPE: peptide (iii) HYPOTHETICAL: NO (iv) ANTI-SENSE: NO (vi) ORIGINAL SOURCE:
  (C) INDIVIDUAL ISOLATE: EE peptide (xi) SEQUENCE DESCRIPTION: SEQ ID NO:1:

```
Glu Val Glu Ala Leu Gln Lys Glu Val Ser Ala Leu Glu Lys Glu Val
1               5                   10                  15
Ser Ala Leu Glu Cys Glu Val Ser Ala Leu Glu Lys Glu Val Glu Ala
                20                  25                  30
Leu Gln Lys
         35
```

(2) INFORMATION FOR SEQ ID NO:2:

(i) SEQUENCE CHARACTERISTICS:
    (A) LENGTH: 35 amino acids
    (B) TYPE: amino acid
    (C) STRANDEDNESS: single
    (D) TOPOLOGY: unknown (ii) MOLECULE TYPE: peptide (iii) HYPOTHETICAL: NO (iv) ANTI-SENSE: NO (vi) ORIGINAL SOURCE:
    (C) INDIVIDUAL ISOLATE: KK peptide (xi) SEQUENCE DESCRIPTION: SEQ ID NO:2:

```
Lys Val Glu Ala Leu Lys Lys Val Ser Ala Leu Lys Glu Lys Val
1               5                   10                  15
Ser Ala Leu Lys Cys Lys Val Ser Ala Leu Lys Glu Lys Val Glu Ala
                20                  25                  30
Leu Lys Lys
         35
```

(2) INFORMATION FOR SEQ ID NO:3:

(i) SEQUENCE CHARACTERISTICS:
    (A) LENGTH: 7 amino acids
    (B) TYPE: amino acid
    (C) STRANDEDNESS: single
    (D) TOPOLOGY: unknown (ii) MOLECULE TYPE: peptide (iii) HYPOTHETICAL: NO (iv) ANTI-SENSE: NO (vi) ORIGINAL SOURCE:
    (C) INDIVIDUAL ISOLATE: EE terminal repeat (xi) SEQUENCE DESCRIPTION: SEQ ID NO:3:

```
Glu Val Glu Ala Leu Glu Lys
1               5
```

(2) INFORMATION FOR SEQ ID NO:4:

(i) SEQUENCE CHARACTERISTICS:
    (A) LENGTH: 7 amino acids
    (B) TYPE: amino acid (C) STRANDEDNESS: single
(D) TOPOLOGY: unknown (ii) MOLECULE TYPE: peptide (iii) HYPOTHETICAL: NO (iv) ANTI-SENSE: NO (vi) ORIGINAL SOURCE:
(C) INDIVIDUAL ISOLATE: EE internal repeat (xi) SEQUENCE DESCRIPTION: SEQ ID NO:4:

Glu Val Ser Ala Leu Glu Lys
1               5

(2) INFORMATION FOR SEQ ID NO:5:

(i) SEQUENCE CHARACTERISTICS:
(A) LENGTH: 7 amino acids
(B) TYPE: amino acid
(C) STRANDEDNESS: single
(D) TOPOLOGY: unknown (ii) MOLECULE TYPE: peptide (iii) HYPOTHETICAL: NO (iv) ANTI-SENSE: NO (vi) ORIGINAL SOURCE:
(C) INDIVIDUAL ISOLATE: KK terminal repeat (xi) SEQUENCE DESCRIPTION: SEQ ID NO:5:

Lys Val Glu Ala Leu Lys Lys
1               5

(2) INFORMATION FOR SEQ ID NO:6:

(i) SEQUENCE CHARACTERISTICS:
(A) LENGTH: 7 amino acids
(B) TYPE: amino acid
(C) STRANDEDNESS: single
(D) TOPOLOGY: unknown (ii) MOLECULE TYPE: peptide (iii) HYPOTHETICAL: NO (iv) ANTI-SENSE: NO (vi) ORIGINAL SOURCE:
(C) INDIVIDUAL ISOLATE: KK internal repeat (xi) SEQUENCE DESCRIPTION: SEQ ID NO:6:

Lys Val Ser Ala Leu Lys Glu
1               5

(2) INFORMATION FOR SEQ ID NO:7:

(i) SEQUENCE CHARACTERISTICS:
(A) LENGTH: 14 amino acids
(B) TYPE: amino acid
(C) STRANDEDNESS: single
(D) TOPOLOGY: unknown (ii) MOLECULE TYPE: peptide (iii) HYPOTHETICAL: NO (iv) ANTI-SENSE: NO (vi) ORIGINAL SOURCE:
(C) INDIVIDUAL ISOLATE: peptide KE, 2EK, Linear 5

( x i ) SEQUENCE DESCRIPTION: SEQ ID NO:7:

Glu Ile Glu Ala Leu Lys Lys Glu Ile Glu Ala Leu Lys Lys
1               5                   10

( 2 ) INFORMATION FOR SEQ ID NO:8:

( i ) SEQUENCE CHARACTERISTICS:
    ( A ) LENGTH: 14 amino acids
    ( B ) TYPE: amino acid
    ( C ) STRANDEDNESS: single
    ( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
    ( C ) INDIVIDUAL ISOLATE: peptide EK, Linear 7

( x i ) SEQUENCE DESCRIPTION: SEQ ID NO:8:

Glu Ile Glu Ala Leu Glu Lys Glu Ile Lys Ala Leu Lys Lys
1               5                   10

( 2 ) INFORMATION FOR SEQ ID NO:9:

( i ) SEQUENCE CHARACTERISTICS:
    ( A ) LENGTH: 14 amino acids
    ( B ) TYPE: amino acid
    ( C ) STRANDEDNESS: single
    ( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
    ( C ) INDIVIDUAL ISOLATE: peptide 2KE, Linear 9

( x i ) SEQUENCE DESCRIPTION: SEQ ID NO:9:

Glu Ile Lys Ala Leu Lys Glu Glu Ile Lys Ala Leu Lys Glu
1               5                   10

( 2 ) INFORMATION FOR SEQ ID NO:10:

( i ) SEQUENCE CHARACTERISTICS:
    ( A ) LENGTH: 14 amino acids
    ( B ) TYPE: amino acid
    ( C ) STRANDEDNESS: single
    ( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
    ( C ) INDIVIDUAL ISOLATE: peptide Linear 10

( x i ) SEQUENCE DESCRIPTION: SEQ ID NO:10:

Glu Ile Gln Ala Leu Lys Lys Glu Ile Gln Ala Leu Lys Lys
1               5                   10

( 2 ) INFORMATION FOR SEQ ID NO:11:

( i ) SEQUENCE CHARACTERISTICS:
    ( A ) LENGTH: 24 amino acids (B) TYPE: amino acid
(C) STRANDEDNESS: single
(D) TOPOLOGY: unknown (ii) MOLECULE TYPE: peptide (iii) HYPOTHETICAL: NO (iv) ANTI-SENSE: NO (vi) ORIGINAL SOURCE:
(C) INDIVIDUAL ISOLATE: exemplary generic library peptide, Fig. 3A (xi) SEQUENCE DESCRIPTION: SEQ ID NO:11:

Glu Ile Glu Ala Leu Lys Lys Glu Ile Xaa Xaa Leu Xaa Xaa Lys Ile
1               5                   10                  15

Xaa Ala Leu Glu Lys Glu Ile Lys
                20

(2) INFORMATION FOR SEQ ID NO:12:

(i) SEQUENCE CHARACTERISTICS:
(A) LENGTH: 24 amino acids
(B) TYPE: amino acid
(C) STRANDEDNESS: single
(D) TOPOLOGY: unknown (ii) MOLECULE TYPE: peptide (iii) HYPOTHETICAL: NO (iv) ANTI-SENSE: NO (vi) ORIGINAL SOURCE:
(C) INDIVIDUAL ISOLATE: LPS epitope library peptide, Fig. 5A (xi) SEQUENCE DESCRIPTION: SEQ ID NO:12:

Glu Ile Glu Ala Leu Lys Lys Glu Ile His Phe Leu Val Gln Lys Ile
1               5                   10                  15

His Ala Leu Glu Lys Glu Ile Lys
                20

(2) INFORMATION FOR SEQ ID NO:13:

(i) SEQUENCE CHARACTERISTICS:
(A) LENGTH: 24 amino acids
(B) TYPE: amino acid
(C) STRANDEDNESS: single
(D) TOPOLOGY: unknown (ii) MOLECULE TYPE: peptide (iii) HYPOTHETICAL: NO (iv) ANTI-SENSE: NO (vi) ORIGINAL SOURCE:
(C) INDIVIDUAL ISOLATE: single-stranded peptide, Fig. 9

(xi) SEQUENCE DESCRIPTION: SEQ ID NO:13:

Glu Ala Glu Ala Ala Lys Lys Glu Ala His Phe Ala Val Gln Lys Ala
1               5                   10                  15

His Ala Ala Glu Lys Glu Ala Lys
                20

(2) INFORMATION FOR SEQ ID NO:14:

(i) SEQUENCE CHARACTERISTICS:
(A) LENGTH: 11 amino acids
(B) TYPE: amino acid

```
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
            ( C ) INDIVIDUAL ISOLATE: linear ZnF peptide, Fig. 9

( x i ) SEQUENCE DESCRIPTION: SEQ ID NO:14:

Lys   His   Phe   Leu   Val   Gln   His   Thr   His   Thr   Gly
    1                       5                             10

( 2 ) INFORMATION FOR SEQ ID NO:15:

( i ) SEQUENCE CHARACTERISTICS:
            ( A ) LENGTH: 26 amino acids
            ( B ) TYPE: amino acid
            ( C ) STRANDEDNESS: single
            ( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
            ( C ) INDIVIDUAL ISOLATE: peptide CP1

( x i ) SEQUENCE DESCRIPTION: SEQ ID NO:15:

Pro   Tyr   Lys   Cys   Pro   Glu   Cys   Gly   Lys   Ser   Phe   Ser   Gln   Lys   Ser   Asp
    1                       5                             10                            15

Leu   Val   Lys   His   Gln   Arg   Thr   His   Thr   Gly
                      20                            25
```